US012778495B2

(12) United States Patent
Ramanathan et al.

(10) Patent No.: US 12,778,495 B2
(45) Date of Patent: Nov. 3, 2026

(54) MULTI-MODAL MEDICAL CONDITION IDENTIFICATION

(71) Applicant: Soliish Inc., Fairfax, VA (US)

(72) Inventors: Narayanan Ramanathan, Aldie, VA (US); Ikshvanku Barot, Suffolk, VA (US); Jatin Maniar, Fairfax, VA (US); Hitesh Kalra, Cupertino, CA (US); Meir Kryger, Hamden, CT (US)

(73) Assignee: Soliish Inc., Fairfax, VA (US)

( * ) Notice: Subject to any disclaimer, the term of this patent is extended or adjusted under 35 U.S.C. 154(b) by 0 days.

(21) Appl. No.: 19/379,270

(22) Filed: Nov. 4, 2025

(65) Prior Publication Data

US 2026/0053433 A1 Feb. 26, 2026

Related U.S. Application Data

(63) Continuation of application No. 18/838,452, filed as application No. PCT/US2024/040376 on Jul. 31, 2024.

(Continued)

(51) Int. Cl.

| | |
|---|---|
| ***A61B 5/00*** | (2006.01) |
| ***G06T 7/00*** | (2017.01) |
| ***G06T 7/60*** | (2017.01) |
| ***G06V 40/10*** | (2022.01) |
| ***G16H 50/20*** | (2018.01) |

(52) U.S. Cl.

CPC .......... *A61B 5/4818* (2013.01); *A61B 5/4547* (2013.01); *A61B 5/4552* (2013.01); *A61B 5/4557* (2013.01); *A61B 5/4561* (2013.01); *A61B 5/4878* (2013.01); *A61B 5/7275* (2013.01); *A61B 5/742* (2013.01); *G06T 7/0012* (2013.01); *G06T 7/60* (2013.01); *G06V 40/15* (2022.01); *G16H 50/20* (2018.01); *G06T 2207/10004* (2013.01); *G06T 2207/20084* (2013.01); *G06T 2207/30004* (2013.01)

(58) Field of Classification Search

CPC ...... A61B 5/107; A61B 5/1077; A61B 5/1079

See application file for complete search history.

(56) References Cited

U.S. PATENT DOCUMENTS

2015/0161331 A1 6/2015 Oleynik
2015/0202395 A1 7/2015 Fromentin (Continued)

*Primary Examiner* — Alyssa M Alter

(74) *Attorney, Agent, or Firm* — Invoke

(57) ABSTRACT

Methods, systems, and apparatus, including computer programs encoded on computer storage media, for medical condition identification. One of the methods includes obtaining visual data representing at least one body part of a subject; obtaining non-visual data that corresponds to one or more biological characteristics of the subject; providing data representing (i) the visual data and (ii) the non-visual data to one or more machine learning models, wherein the one or more machine learning models are trained to predict presence of a medical condition; obtaining an output of the one or more machine learning models that is generated based on the one or more machine learning models processing the visual data and the non-visual data; and determining presence of the medical condition for the subject using the output of the one or more machine learning models.

23 Claims, 8 Drawing Sheets

Related U.S. Application Data

(60) Provisional application No. 63/516,647, filed on Jul. 31, 2023.

(56) References Cited

U.S. PATENT DOCUMENTS

| | | | | |
|---|---|---|---|---|
| 2016/0180587 | A1 | 6/2016 | Bai et al. | |
| 2016/0331301 | A1* | 11/2016 | Radmand | A61B 6/512 |
| 2017/0345155 | A1 | 11/2017 | Higgins et al. | |
| 2019/0117151 | A1* | 4/2019 | Stern | G16H 20/40 |
| 2019/0209405 | A1 | 7/2019 | Sayadi et al. | |
| 2021/0007606 | A1 | 1/2021 | Su et al. | |
| 2021/0217167 | A1 | 7/2021 | Lee et al. | |
| 2021/0327585 | A1 | 10/2021 | Narayanan et al. | |
| 2021/0398655 | A1 | 12/2021 | Evans et al. | |
| 2023/0080929 | A1 | 3/2023 | Lin | |

* cited by examiner

MULTI-MODAL MEDICAL CONDITION IDENTIFICATION

CROSS-REFERENCE TO RELATED APPLICATIONS

This application is a continuation application of, and claims priority to, U.S. patent application Ser. No. 18/838,452, filed on Aug. 14, 2024, and claims the benefit under 35 U.S.C. § 119(e) of the filing date of U.S. Patent Application No. 63/516,647, which was filed on Jul. 31, 2023. The priority applications are incorporated by reference in their entirety.

SUMMARY

This specification describes technologies for improving medical condition determination, e.g., through screening or diagnosis, by using one or more machine learning models, trained using multi-modal data, to predict the presence of a medical condition. Such techniques can reduce equipment and expense incurred by traditional diagnostic methods while providing accurate medical results. The described techniques can facilitate low-cost, non-invasive and easy to administer medical diagnostics. Medical diagnostics can include predictions of medical conditions, such as obstructive sleep apnea, hypertension, risk of stroke, heart attack, or a combination of these, among other medical conditions.

In general, one innovative aspect of the subject matter described in this specification can be embodied in methods that include the actions of obtaining visual data representing at least one body part of a subject; obtaining non-visual data that corresponds to one or more biological characteristics of the subject; providing data representing (i) the visual data and (ii) the non-visual data to one or more machine learning models, wherein the one or more machine learning models are trained to predict presence of a medical condition; obtaining an output of the one or more machine learning models that is generated based on the one or more machine learning models processing the visual data and the non-visual data; and determining presence of the medical condition for the subject using the output of the one or more machine learning models. Other embodiments of this aspect include corresponding computer systems, apparatus, and computer programs recorded on one or more computer storage devices, each configured to perform the actions of the methods.

The foregoing and other embodiments can each optionally include one or more of the following features, alone or in combination. In particular, one embodiment includes all the following features in combination. Feature 1: Obtaining the visual data representing the at least one body part of the subject comprises: obtaining an image representing the face of the subject. Feature 2: Obtaining the visual data representing the at least one body part of the subject comprises: obtaining a first image representing a first body part of the subject from a first view perspective; and obtaining a second image representing a second body part of the subject from a second view perspective. Feature 3: The first body part is the same as the second body part. Feature 4: The first body part is different from the second body part. Feature 5: Obtaining the visual data representing the at least one body part of the subject comprises: capturing image data from a front facing camera of a smartphone during a relative motion between the smartphone and the at least one body part of the subject—e.g., where relative motion can include a smartphone moving in a substantially circular motion, a smartphone remaining stationary and a subject moving, or a smartphone moving and a subject remaining stationary. Feature 6: Determining the presence of the medical condition comprises: determining the presence of a sleep apnea condition. Feature 7: Determining the presence of a sleep apnea condition comprises: determining the presence of an obstructive sleep apnea condition. Feature 8: Determining the presence of the medical condition comprises: determining the presence of at least one of a hypertension condition or cardiovascular disease. Feature 9: Obtaining the visual data representing the at least one body part of the subject comprises: obtaining visual data representing an oral cavity of the subject. Feature 10: Obtaining the visual data representing the at least one body part of the subject comprises: obtaining visual data representing a craniofacial region. Feature 11: Obtaining the visual data representing the at least one body part of the subject comprises: obtaining visual data representing an anterior cervical region. Feature 12: Obtaining the visual data representing the at least one body part of the subject comprises: obtaining a first image of a front of a hand of the subject; and obtaining a second image of a back of the hand of the subject. Feature 13: Actions include providing a cue for obtaining the visual data. Feature 14: Providing the cue for obtaining the visual data comprises: providing one or more of an audio cue or a visual cue. Feature 15: Providing the audio cue comprises: activating a speaker to provide a language-based cue. Feature 16: Providing the cue for obtaining the visual data comprises: providing an outline on a display of a body part corresponding to the at least one body part of the subject. Feature 17: Obtaining the non-visual data comprises: obtaining results of a questionnaire taken by the subject. Feature 18: The questionnaire taken by the subject comprises a custom questionnaire prepared for the subject, and actions include: prior to obtaining one or more items of the results, modifying a preexisting questionnaire based on data representing the subject to generate the custom questionnaire for the subject. Feature 19: Actions include generating a first embedding representing at least a portion of the visual data; generating a second embedding representing at least a portion of the non-visual data; and generating a fused data set that combines the first embedding and the second embedding, wherein providing the data representing (i) the visual data and (ii) the non-visual data to the one or more machine learning models comprises: providing the fused data set to the one or more machine learning models. Feature 20: Providing the data to the one or more machine learning models comprises: providing the data representing the visual data to a convolutional neural network (CNN); and providing the data representing the non-visual data to a recurrent neural network (RNN). Feature 21: Actions include in response to determining presence of the medical condition for the subject, generating recommendation data for one or more therapeutic interventions; and transmitting the recommendation data to an electronic device. Feature 22: Obtaining the visual data representing the at least one body part of the subject comprises: obtaining an image of a particular body part; and extracting one or more features from the image of the particular body part, wherein the visual data includes the extracted one or more features. Feature 23: Extracting the one or more features from the image of the particular body part comprises: extracting points representing a face of the subject, and wherein obtaining the visual data comprises: generating, using the extracted points, a face model of the subject. Feature 24: Obtaining the non-visual data comprises: obtaining audio data of the subject speaking. Feature 25: Obtaining the audio data comprises: obtaining first audio of the subject speaking; and obtaining second audio of the subject speaking with a speech restriction. Feature 26: Obtaining the second audio of the subject speaking with the speech restriction comprises: obtaining audio while a nasal passage of the subject is restricted. Feature 27: Actions include training the one or more machine learning models using (i) a set of training data representing a number of subjects and (ii) a set of ground truths representing known medical conditions for each of the number of subjects. Feature 28: Actions include generating the set of ground truths, wherein generating the set of ground truths comprises: obtaining a set of medical reports that include data indicating the medical conditions for each of the number of subjects; and providing the set of medical reports to a trained language model. Feature 29: Actions include generating an embedding for at least a portion of the set of medical reports; and storing the embedding for at least the portion of the set of medical reports in memory, wherein obtaining the set of medical reports that include data indicating the medical conditions for each of the number of subjects comprises: querying the memory for the embedding representing at least the portion of the set of medical reports.

In general, another innovative aspect of the subject matter described in this specification can be embodied in methods that include the actions of receiving an input selecting a medical condition from a plurality of medical conditions available for diagnosis; in response to receiving the input, accessing stored data corresponding to the plurality of medical conditions and a plurality of machine learning models that are configured to determine presence of the plurality of medical conditions; obtaining from the stored data, using the received input, data corresponding to the selected medical condition and at least one trained machine learning model that is configured to determine presence of the selected medical condition; providing medical data representing a subject to the at least one trained machine learning model; and determining presence of the selected medical condition for the subject using output of the at least one trained machine learning model, wherein the output of the at least one trained machine learning model is generated based on the at least one trained machine learning model processing the medical data. Other embodiments of this aspect include corresponding computer systems, apparatus, and computer programs recorded on one or more computer storage devices, each configured to perform the actions of the methods.

The foregoing and other embodiments can each optionally include one or more of the following features, alone or in combination. In particular, one embodiment includes all the following features in combination. Feature 1: Actions include receiving a second input selecting a different second medical condition from the plurality of medical conditions available for diagnosis; in response to receiving the second input, obtaining from the stored data using the second input, second data corresponding to the second medical condition and a trained second machine learning model that is configured to determine presence of the second medical condition, wherein at least one of the second data or the trained second machine learning model is respectively different from the data corresponding to the selected medical condition or the at least one trained machine learning model configured to determine presence of the selected medical condition; providing second medical data representing a second subject to the trained second machine learning model; and determining presence of the second medical condition for the second subject using output of the trained second machine learning model, wherein the output of the trained second machine learning model is generated based on the trained second machine learning model processing the second medical data. Feature 2: The first subject and the second subject are the same subject.

The technology described in this specification can be implemented so as to realize one or more of the following advantages. For example, the described techniques reduce the expense and equipment typically incurred for medical condition diagnosis, such as sleep apnea diagnosis. Instead of traveling to specific clinics or medical professionals for diagnostics, subjects can provide data, using techniques described, to one or more trained machine learning models. The machine learning models can be trained to identify one or more medical conditions using the provided data.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
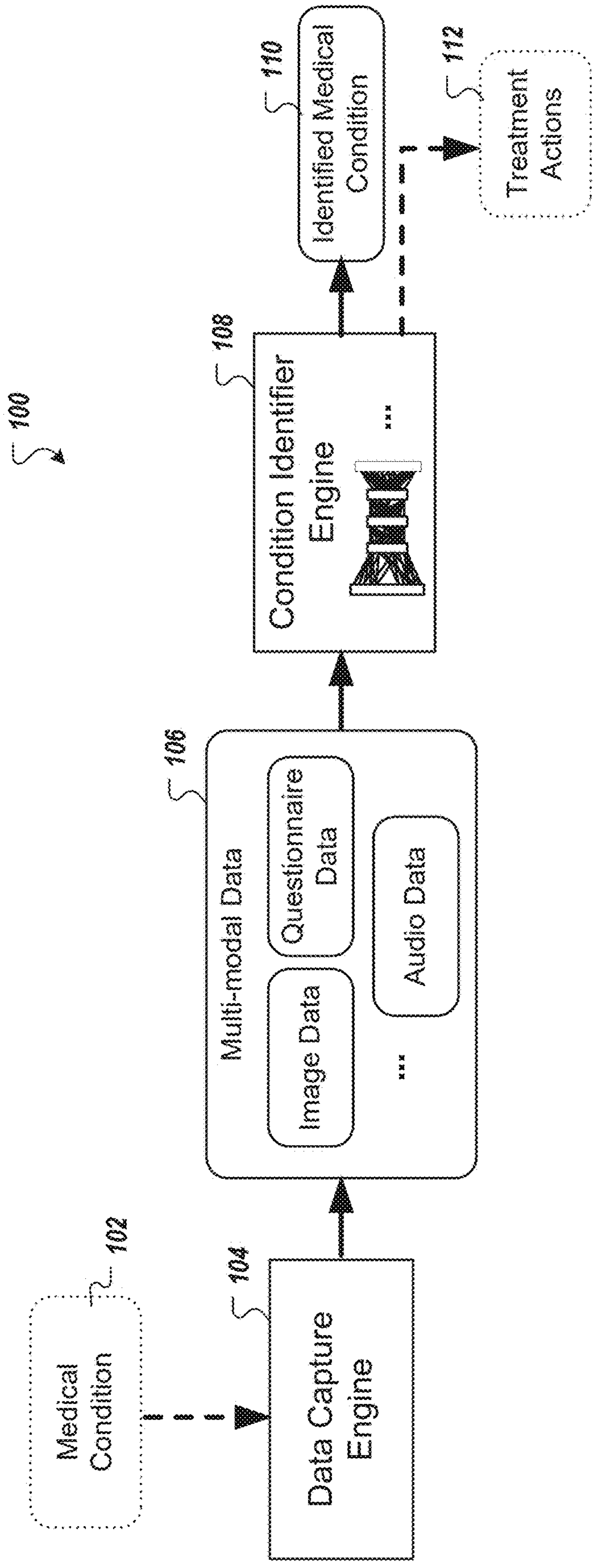
FIG. 1 shows an example medical condition determination system.

This specification describes techniques for improving medical screening, diagnosis and support by using one or more machine learning models, trained using multi-modal data, to predict the presence of a medical condition. Such techniques can reduce equipment and expense incurred by traditional diagnostic methods while providing accurate medical results. The described techniques can facilitate low-cost, non-invasive and easy to administer medical diagnostics. Medical screening and/or diagnostics can include predictions of medical conditions, recommendations for therapeutic pathways, or both. The medical conditions include obstructive sleep apnea, hypertension, pulmonary hypertension, risk of stroke, cardiovascular disease, Type 2 Diabetes, depression, anxiety, or a combination of these among others.

As one exemplary application, in some cases, the techniques can be used to predict the likelihood of a person suffering from sleep apnea, such as OSA. Obstructive Sleep Apnea (OSA), a condition characterized by the partial or complete obstruction of the upper airway during sleep, when left untreated is known to have a significant impact on cardiovascular health, heart disease, leading to hypertension, irregular heart rhythms and increased risk of strokes. Intermittent hypoxia and sleep fragmentation, both associated with OSA, have been shown to disrupt glucose metabolism thereby increasing the risk of developing type-2 diabetes, impairing cognitive performance, increasing risks of depression and decreasing overall quality of life. While generally prevalent in middle-aged and older adults, among men, among obese subjects, and increasingly among certain ethnic groups (African American, Mexican, South Asian), OSA has also been observed in children and in pregnant women. Screening for OSA enables detection and early intervention through therapy, lifestyle modifications, and surgeries.

OSA can be a debilitating sleep disorder that affects an estimated 26% of US adults between the ages of 30 and 70. OSA is a heterogenous condition that can emerge from numerous comorbidities and anatomical variations. Rates of OSA prevalence, diagnosis, and care are not homogenous across patient demographics. While several of the strongest OSA risk factors have an established genetic basis, notable risk factors can include environmental or social exposures and demographic classifications (e.g., sex, age, gender, race or ethnicity). OSA prevalence can vary widely across patient demographics, e.g., as children, African Americans are 4-6 times more likely to suffer from OSA than white patients; observed OSA severity is more than 20% greater in African Americans; and elderly African Americans are more than 2.1 times more likely to have severe OSA compared to white patients of a similar age. Other groups disproportionately affected by OSA include Southeast Asians, Hispanics, and Native Americans. Despite the imbalance in OSA epidemiology, patients of disproportionately affected demographics are generally less likely to have access to OSA care than others, e.g., white counterparts.

Polysomnography (PSG), an overnight sleep study conducted at sleep laboratory settings is considered the de-facto gold standard for diagnosing OSA. In conjunction with PSG, physicians adopt EKG, EEG and MRI to measure electrical activities of the heart and the brain, and to study potential structural abnormalities in the upper airway anatomy that contribute to OSA. Such diagnostic procedures present challenges in terms of their availability and affordability to the larger population. Home Sleep Apnea Testing (HSAT) involving portable monitoring devices and Sleep Questionnaires have been used for uncomplicated cases to assess the likelihood of OSA. However, these procedures capture far fewer parameters than needed for accurate diagnosis, leading to inaccuracies or subjective interpretations of data gathered. Further, HSAT may be impacted by factors such as improper sensor placement, patient non-compliance, and interference from external factors thereby affecting its overall reliability.

The disclosed techniques can include gathering multimodal data from subjects. Multimodal data can include imagery and video capturing the subjects' cervico-craniofacial complex from different viewpoints, voice samples that help assess their tonal quality while uttering a set of preselected phrases, or sleep questionnaires that gather data on their sleep quality and medical history, or a combination of these among others. Multimodal data can include oral cavity imagery, such as images representing lower teeth, upper teeth, upper palate, tongue, underside of the tongue, posterior pharyngeal wall, or a combination of these among others. Multimodal data can include generated content from applications, data captured from wearable devices, such as watches, rings, or other wearables, or data from testing equipment, such as SPO2 sensors.

In some implementations, techniques include capturing imagery and video gathered from within the subject's oral cavity. Factors such as recessed jaw, facial asymmetry, maxillary insufficiency, mandibular insufficiency, increased neck circumference, increased tendency towards oral breathing can indicate constrictions in the upper airway anatomy that contribute to OSA. Factors can include other data, such as data indicating enlarged tonsils, enlarged tongue, crowding of the teeth, high arched palate, bruxism, or a combination of these, among others.

In some implementations, techniques include learning models—such as supervised deep learning models or other types of machine learning models—that process multimodal data. For example, the learning models can leverage the power of fusion in convolutional neural networks to combine and process multimodal data (e.g., as and when available) for effective detection of a medical condition and characterization of the onset of the medical condition.

In some cases, a system can facilitate multimodal data collection. For example, a system can include software to capture data (e.g., text, voice, image, video) of subjects. The system can use the data to help screen subjects for one or more medical conditions, such as OSA, high blood pressure, diabetes, heart disease, abnormal heart rhythm, stroke, or a combination of these among others. In some implementations, one or more parameters of the system can be adjusted by a user or system administrator to select one or more different medical conditions. The system can accordingly be configured to collect and analyze data corresponding to the selected medical condition(s).

In some implementations, learning-based models can be developed based on data gathered by the system and ground truth labels. In some implementations, ground truth labels are provided by a physician. Additionally or alternatively, in some implementations, ground truth labels are retrieved from electronic health records, or. obtained from polysomnography test results or other test output. In some implementations, ground truth labels are generated by one or more computer algorithms. Once one or more models have been trained, the system can operate as a screening application. The system can perform data collection, e.g., before, during, or after, a screening operation.

The techniques described can be used across the general population, across age groups, and does not exclude medical assessment on individuals with comorbidities. With learning techniques, such as deep learning attribution techniques, integrated, the described techniques can reduce subjective decision making and increase accuracy and efficiency in detection of medical conditions, such as OSA or other conditions.

FIG. 1 shows an example medication condition determination system 100. The system 100 includes a data capture engine 104 and a condition identifier engine 108. In general, the system 100 captures multi-modal data, such as multimodal data 106, and generates an identified medical condition 110. The multi-modal data 106 can include image data, questionnaire data, audio data, or a combination of these among others. The multi-modal data 106 can include generated data, such as data from applications, questionnaires, or wearable sensors. The identified medical condition 110 can include a score indicating a likelihood that a subject has a particular medical condition, such as medical condition 102.

In some cases, the data capture engine 104 captures data in a sequence. For example, the data capture engine 104 can capture a first item of data and then, in response to successfully capturing the first item of data, capture a second item of data. The data capture engine 104 can capture data in a sequence to generate the multi-modal data 106. For example, the data capture engine 104 can obtain questionnaire data, e.g., by prompting a user for audio or textual responses to one or more questions. Following obtaining of questionnaire data, the data capture engine 104 can obtain one or more scans of a subject's body, e.g., images or video of a subject's head. Images or video of a subject's head can include images of a subject's oral cavity. After obtaining the body scans, the data capture engine 104 can obtain audio of a subject, e.g., an audio recorded using a microphone of the data capture engine 104 of a subject speaking a word or phrase.

In some cases, a sequence of body scans can include one or more of: a scan of a subject's head looking at the camera, a left side profile, a right side profile, or an upward looking pose. An upward looking pose can include a scan inside the mouth to intramural cavity assessment. In general, the data capture engine 104 can capture images of a subject's body in any number of different poses. Each body pose can be captured as image or video data and can be included in the multi-modal data 106 for processing.

In some cases, the data capture engine 104 captures data in alternative sequences. For example, the data capture engine 104 can capture audio recordings, followed by images, followed by questionnaire data. The data capture engine 104 can capture a single modality of data and generate the multi-modal data 106 from a single model of data, e.g., a set of visual images or video taken of a subject's body. In general, the data capture engine 104 can capture different data, e.g., different sequences of data capture or different modes of data, for different medical conditions to be identified.

In some cases, the data capture engine 104 captures data without instigation or involvement by a user, (e.g., a subject or a medical professional). For example, the data capture engine 104 can obtain data from electronic health records or other medical data from another system. In some cases, the data capture engine 104 invokes one or more application programming interface (API) service calls to obtain data. The data capture engine 104 can perform one or more pre-screening operations. For example, the data capture engine 104 can obtain one or more health records, e.g., from a dataset of one or more health records, and parse the data, e.g., to identify likely candidates with a risk of a medical condition, such as OSA. The system 100 can then generate a notification or interface to engage with identified persons at risk for a medical condition, e.g., based medical data, such as images, medical history, or a combination of these among others.

In some cases, the data capture engine 104 obtains an indication of a medical condition to be identified. For example, the data capture engine 104 can obtain the medical condition 102. The data capture engine 104 can be configured to capture data for multiple different medical conditions. The data capture engine 104 can be configured to adjust a process of data capture depending on the medication condition obtained. For example, if the medical condition 102 is sleep apnea, the data capture engine 104 can be configured to capture data indicative of sleep apnea. If the medical condition 102 is cardiovascular disease, the data capture engine 104 can be configured to capture data indicative of cardiovascular disease. In general, the data capture engine 104 can capture any type of data that is indicative of a medical condition, such as the medical condition 102.

In some cases, the data capture engine 104 includes guided data collection. For example, the data capture engine 104 can be configured to activate speakers to play a voice that instructs a subject to obtain data. For example, the data capture engine 104 can activate speakers to play a recording or computer-generated voice that says, "face the camera and position your head within the outline displayed on the screen," e.g., for a case where a device for data capture includes a screen and a camera, such as a smartphone, laptop, or desktop computer with connected peripheral devices. The data capture engine 104 can be configured to display visual indicators to help a subject obtain data. For example, the data capture engine 104 can be configured to display an outline of a head on a screen facing a subject that is also showing a live feed of the subject. The display can be the display of a smartphone and the camera capturing video of the subject can be a front facing camera of the smartphone. In some cases, the data capture engine 104 activates audio or visual cues to guide a subject to have a particular facial expression, such as a neutral facial expression.

In some implementations, the data capture engine 104 includes a head pose estimator process. For example, the data capture engine 104 can use one or more visual detection machine learning models to identify features of a subject's face captured in one or more captured images. The data capture engine 104 can determine whether measurements satisfy one or more thresholds. For example, the data capture engine 104 can determine if roll, pitch, yaw or other angles of a subject's head satisfy one or more thresholds or are within one or more value ranges. In response to the data capture engine 104 determining that measurements satisfy one or more thresholds, the data capture engine 104 can capture one or more additional images while a subject maintains a current head pose. In some cases, the data capture engine 104 can prompt, e.g., using voice or visual prompts, the subject to remain still for additional image captures. In some cases, the data capture engine 104 captures video.

In some cases, the data capture engine 104 captures images in a buffer and removes images that do not yield measurements that satisfy one or more thresholds. For example, the data capture engine 104 can capture one or more images using one or more cameras. The data capture engine 104 can run a head pose estimator on one or more of the captured images. The data capture engine 104 can determine whether or not the measurements satisfy one or more thresholds. In response to the measurements not satisfying the one or more thresholds, the data capture engine 104 can remove the one or more captured images from memory, e.g., an image buffer. In response to the measurements satisfying the one or more thresholds, the data capture engine 104 can retain the corresponding one or more images for further processing, e.g., by one or more models for medical condition identification. By storing images in the buffer, the data capture engine 104 can reduce an amount of time a subject has to maintain a given pose.

In some cases, the data capture engine 104 obtains neutral expressions of a subject. For example, the data capture engine 104 can identify and obtain frames with a subject's face. The data capture engine 104 can process the frames, e.g., running a fiducial feature extractor on the subject's face. The data capture engine 104 can monitor for a subset of features, such as features around the eyes or mouth. If the subset of features indicates the subject is not in a neutral state, the data capture engine 104 can provide a notification to the subject to make a corresponding change to their facial expression. If a subject's eyes are closed or if eyes are not detectable (e.g., because subject is wearing glasses) or if mouth is not in a neutral state, the data capture engine 104 can flag the frame can either not use it for medical condition determination or can prompt a subject or user for additional data, such as a new image to be taken.

In some cases, the data capture engine 104 notifies a subject to correct an element of data capture to improve data capture quality. For example, the data capture engine 104 can activate speakers to notify a subject to center their face within one or more captured images. The data capture engine 104 can display visual indicators on a screen directing a subject to change a head position, e.g., so that portions of the head indicative for a medical condition diagnosis are more visible.

In some cases, the data capture engine 104 is configured to capture data indicating craniofacial features, anterior cervical features, intraoral cavity features, or a combination of these among others. For example, the data capture engine 104 can be configured to direct a subject to obtain images of their head. The data capture engine 104 can use activated speakers or display elements to direct a user. In some cases, display elements indicate a scale, e.g., distance to camera) at which images or video is preferably taken. The data capture engine 104 can illustrate sub-optimal images to inform a subject how not to obtain data, e.g., showing a representation of a subject capturing images at the wrong distance or in dim lighting conditions, among others.

In some cases, the data capture engine 104 guides—e.g., using audio or visual cues—a subject to raise their chin such that their neck is largely visible to a camera. Desired neck position can be illustrated on a screen—e.g., by an avatar, actor, or other visual indication. Head pose can be estimated by the data capture engine 104 using a head pose detector. Once measurements of one or more images—e.g., roll, pitch, yaw angles—satisfy one or more threshold requirements (such as the angles being in a range desired for 'chin-up neck shots'), the data capture engine 104 can prompt the subject to remain still. The data capture engine 104 can gather additional one or more images as the subject remains still. In some cases, the data capture engine 104 stores images as the subject is positioning themselves corresponding to the cues and, once it obtains an image where one or more angles or features of the image satisfy one or more thresholds, the data capture engine 104 can store the corresponding one or more images for processing without requiring the subject to hold a pose for an extended period of time. Images can be recorded periodically while a subject is in frame. Once an image satisfies one or more threshold requirements—e.g., angles of the head satisfy one or more angle thresholds—an image can be saved for processing without further delay or pose holding by the subject. Other poses of a body, such as poses of the head or other body parts, such as a hand, wrist, leg, arm, among others, can be captured by the data capture engine 104 in a similar manner.

In some cases, the data capture engine 104 notifies a subject if one or more captured images do not satisfy one or more quality thresholds. For example, the data capture engine 104 can capture one or more images using one or more cameras and determine one or more quality factors, such as pose angles, brightness, distance to camera, or a combination of these among others. The data capture engine 104 can determine if one or more quality factors do not satisfy one or more thresholds. For example, the data capture engine 104 can determine that a brightness threshold is not satisfied if a subject captures an image in a dark room. In response to the data capture engine 104 determining that one or more quality factors do not satisfy one or more thresholds, the data capture engine 104 can notify the subject. For example, the data capture engine 104 can notify the subject that one or more quality factors have not satisfied one or more thresholds. The data capture engine 104 can notify the subject to make one or more alterations to a data capture to improve the quality factors, e.g., turn on a light in the room. Notifications can include visual or auditory cues.

In some cases, the data capture engine 104 provides a questionnaire. For example, the data capture engine 104 can generate and provide for display a set of one or more questions and an interface configured to allow a subject to provide answers to the one or more questions, such as radio buttons or textboxes. The questions can be a predetermined list, e.g., obtained from a server communicably connected to the data capture engine 104. In some cases, the data capture engine 104 generates questions using one or more generative models. For example, the data capture engine 104 can include a generative model configured to ask questions for a particular subject or a particular medical condition. In some cases, the questions can be designed to illicit one or more indicators of a medical condition.

In some cases, a subject's demographic information can be used to adapt questions. In some cases, based on prior responses, a system can opt to skip one or more questions. In some cases, the system 100 uses generative models to ask questions. For example, the system 100 can use previously obtained data to personalize a set of questions, e.g., using a generative model, such as a language model. If abnormal features are present in the data, the system 100 can include questions to illicit responses to further describe those features, potentially eliciting underlying diseases or conditions related to a medical condition to be determined for a subject.

In some cases, the data capture engine 104 provides questions to prompt a yes or no response from a subject. For example, the data capture engine 104 can provide a question that asks a subject: "have you been told that you snore," e.g., in an example case for identifying a medical condition of sleep apnea. The data capture engine 104 can store results for yes/no questions in binary format where 0 represents yes/no and 1 represents the response not represented by 0, e.g., 0 can represent no and 1 can represent yes. In some cases, such storage can effectively compress the captured data—e.g., where traditional responses might be recorded using string or integer values which occupy multiple bytes.

In some cases, a sleep questionnaire include one or more of the following questions: "what is your height?", "what is your weight?", "have you been told that you snore?", "do you feel tired or sleepy during the day?", "do you have any trouble falling or staying asleep?", or "do you have any one or more of the following conditions:" where conditions can include, e.g., high blood pressure, diabetes, heart disease, abnormal heart rhythm, stroke.

In some cases, the data capture engine 104 requests subjects to provide a voice sample. For example, the data capture engine 104 can use visual or auditory cues to direct a subject to speak a word or phrase (e.g., one that captures one or more intonations). In some cases, the data capture engine 104 requests that a subject speak with a modification. For example, the data capture engine 104 can request that a subject speak a word or phrase while pinching their nose or performing other actions to modify the speech to provide additional data for processing. The data capture engine 104 can capture voice data representing a subject speaking a word or phrase with a modification and without a modification. The data capture engine 104 can use one or more microphones to capture a subject speaking a word or phrase.

In some cases, the data capture engine 104 prompts a subject to present their oral cavity area. For example, the data capture engine 104 can prompt a subject to open their mouths wide and say "aahh". The data capture engine 104 can use voice or visual cues to help improve data capture. In some cases, the data capture engine 104 can capture video (e.g., approximately 5 seconds) of a subject's oral cavity. The video can include representations of tonsils, tongue, teeth arrangement, how arched the palate is, among other features of the subject.

In some cases, the data capture engine 104 uses a subject who self-captures data, e.g., using a front facing camera of a device, such as a smartphone. In some cases, the data capture engine 104 uses a third party assisted system to capture data for a given subject. For example, a mechanism or a third-party person can help obtain data, e.g., using a rear facing camera of a device or specialized medical equipment. In general, data capture can be self-administered or administered by a medical professional.

In some cases, a number of oral features captured in images of an oral cavity are analyzed using one or more models. For example, features can include one or more of: enlarged tonsils, elongated uvula, soft palate, Mallampati score (e.g., visibility of oropharynx), tongue size or position, narrow dental arches, retrognathia or micrognathia, crowded oropharynx, bruxism, mouth breathing (e.g., indication of dry mouth, inflamed gums, or other indications). In some cases, the system 100 can use oral cavity features to determine one or more output results, such as a likely medical diagnosis. The system 100 can include elements to prompt a user to display portions of their oral cavity. Prompts can include directing a subject to stick their tongue out, open mouth and direct camera of the data capture engine 104 on a lower, upper, back, or other parts of the mouth (e.g., lower teeth, upper teach, upper palate, uvula, tonsils, opening to pharynx, among others). In general, the data capture engine 104 can detect one or more malocclusions.

In some cases, the data capture engine 104 identifies an optimal frame of one or more images captured. For example, the data capture engine 104 can use one or more analyzing processes to determine an image that is most conducive to accurate detections, such as sharpness detection, centering and alignment, contrast or edge detection, or a combination of these among others. In some cases, data captured is pre-processed before being provided to the condition identifier engine 108. For example, data can be provided to one or more models, such as a convolutional neural network, to extract features from the data. The extracted data can be included in input data, such as the multi-modal data 106, for the condition identifier engine 108.

In some cases, the data capture engine 104 includes a device used by a medical professional. For example, a medical professional can use a smartphone that captures image of a patient. The data can be used by the system 100 to provide a likely medical diagnosis, or a set of potential medical diagnosis, for review by the medical professional. In some cases, multiple diagnoses can be provided to subjects for review by the subjects.

In some cases, the data capture engine 104 obtains data indicating a subject's tendency towards oral breathing versus nasal breath. For example, the data capture engine 104 can capture image data indicating an openness of a subject's mouth during rest state. In some cases, the data capture engine 104 can perform face detection using one or more images of a subject. For example, the data capture engine 104 can fit a three-dimensional face model to a captured image representing a face of the subject. In some cases, a face model can include a dense set of vertices identified on a subject's face, e.g., a subject's mouth. Coordinates of such vertices (such as x, y, and z coordinates) can be used to detect instances when a subject's mouth was open or closed, e.g., when a subject is sleeping. The data capture engine 104 can include a sensor that is activated during a subject's sleep, e.g., to capture one or more images. For example, a subject can prop a camera of the data capture engine 104 to face themselves while the subject sleeps. In general, data indicating that a subject's mouth is open while sleeping can indicate that the subject has a higher likelihood of oral breathing which can be correlated with sleep apnea or other medical conditions.

In some cases, the data capture engine 104 includes one or more wearable or mobile devices. For example, the data capture engine 104 can capture data indicating health behavioral data, otherwise referred to as lifestyle data. In some cases, the data capture engine 104 captures one or more of the following: sleep patterns, physical activity, or body weight and body composition. For example, a wearable device or mobile device of the data capture engine 104 can include sleep tracking features, e.g., that can monitor one or more of sleep duration, quality, disruptions, irregularity in sleep patterns, decreased sleep efficiency, snoring, or frequent nighttime awakenings. A wearable device or mobile device of the data capture engine 104 can capture data indicating physical activity levels of a subject—e.g., step counts, accelerometer data, elevation change data, GPS pings, among others. Decreased physical activity can increase the likelihood of certain medical conditions, such as sleep apnea. In some implementations, a wearable device measuring various data for a subject, such as heart rate, blood oxygen level, blood pressure, disturbances to sleep, body movements during sleep, among others, can provide data to, or as part of, the data capture engine 104. A wearable device or mobile device of the data capture engine 104 can capture data representing body weight or body composition. A wearable device or mobile device of the data capture engine 104 can track body weight, body mass index, or body composition trends which can, e.g., be correlated with one or more risks of medical conditions.

In some cases, the data capture engine 104 captures biological vital readings. For example, the data capture engine 104 can capture heart rate, blood oxygen levels, or glucose levels. In some cases, a wearable device or mobile device of the data capture engine 104 can capture biological vital readings. A subject can provide permission to obtain data from one or more devices, such as wearable or mobile devices. A duration window for data collections by the data capture engine 104 can span days, weeks, months, among other time increments (e.g., the most recent few weeks).

In some cases, the system 100 adjusts data capture, e.g., based on a likelihood of a medical condition. For example, the system 100 can adjust a granularity of a sleep questionnaire or a number of data types captured from a subject based on their OSA likelihood, their comorbidities, their prior health conditions, among other factors. The system 100 can serve the purpose of gathering useful information that can help diagnose medical conditions, such as OSA, with more accuracy. The system 100 can be used to identify one or more underlying factors that can lead to a medical condition, such as OSA. In some cases, the more serious a medical condition is anticipated to be (e.g., based on factors determined by the condition identifier engine 108 or obtained by the data capture engine 104), the more data points that are gathered by the data capture engine 104.

In some cases, the data capture engine 104 provides a subject with a choice of data streams to provide. The data-types that the data capture engine 104 can obtain from a subject may vary from one subject to another, e.g., due to various reasons such as (i) personal preference or permissions, (ii) lack of access to equipment needed for data capture (e.g., microphone or camera), (iii) subject might not have sufficient time to provide all data, (iv) an environment the subject is submitting data from might not be conducive for certain types of data collection.

In some cases, the data capture engine 104 includes one or more models trained to determine a level of a medical condition risk. For example, the data capture engine 104 can include a model trained on one or more data types to predict a risk of a medical condition, such as OSA. In response to a subject's risk satisfying one or more risk thresholds, the data capture engine 104 can provide an interface for capturing additional data. For example, if the data capture engine 104 determines that a subject is at a high risk based on one or more detected factors of OSA, then the data capture engine 104 can provide an interface for the subject to provide additional data, e.g., for a more thorough analysis. Additional data can help the system combine data from multiple streams and can help improve accuracy of medical condition identification, risk model predictions, attribution predictions, among others.

In some cases, a risk model of the data capture engine 104 is trained on different data than one or more medical condition detection models of the condition identifier engine 108. For example, a risk model of the data capture engine 104 can be trained on data that is relatively easy to provide, such as questionnaire data or data from connected devices such as wearables or mobile devices. In this way, the system 100 can reduce an amount of time subjects spend submitting data by requiring only high risk subjects to provide substantial data and allowing low risk subjects to provide less data.

The condition identifier engine 108 obtains the multimodal data 106 generated by the data capture engine 104. In some cases, the condition identifier engine 108 includes data preprocessing stages. In some cases, the condition identifier engine 108 includes feature extraction processing stages.

The condition identifier engine 108 generates output, e.g., the identified medical condition 110, treatment actions 112, or a combination of these among others. In some cases, the condition identifier engine 108 enables a personalized medicine approach, e.g., through personalized output based on captured data of a given subject. In some cases, the condition identifier engine 108 generates the treatment actions 112 that include, e.g., one or more therapy pathways, such as Oral appliance Therapy, CPAP, electric stimulation implant, pharmaceutical interventions, or a combination of these among others. For example, the system 100 can obtain data of a subject with mild to moderate OSA. Based on captured data of the subject, e.g., calculation of craniofacial or oral cavity analysis, the system 100 can recommend that the subject is a good candidate for oral appliance therapy. In some cases, the system 100 recommends treatment based on measured compliance rates. For example, the system 100 can recommend that the subject is a good candidate for oral appliance therapy as the system 100 may determine, based on one or more stored or obtained values indicating compliance for one or more treatments, that the oral appliance therapy has better compliance than CPAP. Therefore, the system 100 can include oral appliance therapy in output, such as the treatment actions 112.

In some cases, the condition identifier engine 108 preprocesses obtained face images (e.g., frontal, profile, or other views of a subject's face obtained by a camera of the data capture engine 104). For example, the condition identifier engine 108 can include one or more of the following processing elements: (i) a face detector, (ii) fiducial feature extractor, e.g., on a craniofacial complex of a subject, or (iii) a fiducial feature extractor, e.g., on an anterior cervical region of a subject.

In some cases, preprocessing includes performing operations of a face detector on one or more images obtained by the data capture engine 104. For example, the condition identifier engine 108 can perform face detection using one or more trained models of a face detector to determine one or more regions that represent a face in one or more images. In some cases, the preprocessing can output a bounding box with coordinates (e.g., x1, y1, x2, y2). The bounding box can bound a representation of a face in one or more images.

In some cases, the condition identifier engine 108 includes a deep learning model. For example, the deep learning model can be trained to fit face models, such as three-dimensional face models, to images that include faces, such as two-dimensional face images. The fitted face models can include a face mesh that includes a dense set of vertices fit onto the obtained image of a subject's face. The face image can include one or more face poses, such as frontal or sagittal. From within the dense set of fitted vertices, a set of fiducial landmarks can be used—e.g., those used for face anthropometric studies.

Fiducial points on a subject's face can be used for feature localization or face registration. The condition identifier engine 108 can identify a dense set of feature locations using images of a face. The condition identifier engine 108 can extract measurements from the face (e.g., both 2D measurements and 3D measurements, if a fitted face mesh provides X, Y, Z locations for every feature point identified or locations that satisfy one or more accuracy thresholds). The measurements can be used by the condition identifier engine 108 to estimate relative positionings of facial features, such as mid-face or lower face, retrognathic mandible, prognathic maxilla, among others.

In some cases, the condition identifier engine 108 includes models that are trained using a vision library that specializes in the detection of fiducial features and edges in the anterior cervical region. Face detection algorithms are typically trained to detect features of the craniofacial complex—e.g., the head, face, and oral cavity. In contrast, the anterior cervical region can include a neck of a subject—e.g., below inferior border of the mandible and above the jugular and clavicular notch of the manubrium. One or more models of the condition identifier engine 108 can be trained to detect features within the anterior cervical region. A training library used for such training can include labeled ground truth images that represent silhouettes in an anterior cervical region and fiducial features corresponding to the menton and cricoid elements in the anterior cervical region.

A training library for one or more models of the condition identifier engine 108 can include data obtained by one or more subjects or previously prepared data—e.g., from online image datasets or artificially generated data, such as artificially generated anterior cervical region data. In some cases, a subject obtains data for training. For example, a subject can present a cervico-craniofacial complex from multiple viewpoints: covering one or more of frontal, facing left, or facing right. "Facing left" and "facing right" can mean different things for different people, e.g., based their neck mobility.

In some cases, one or more models of the condition identifier engine 108 generate face meshes using obtained face images. For example, a model can generate a three-dimensional face mesh for each face represented in one or more images. N number of points can be extracted for all points of fit. Each point can include one or more coordinates (e.g., x, y, and z). Face meshes extracted by the condition identifier engine 108 can be integrated into a single face mesh for a given subject.

Face mesh integration can be performed by the condition identifier engine 108. Face mesh integration can include integrating three-dimensional face mesh points where two coordinate values (e.g., x,y) correspond to feature coordinates on a frontal plane and a third coordinate value (e.g., z) corresponds to a feature depth (such as a sagittal plane). In some cases, the coordinates corresponding to the frontal plane can be better estimated when the face is near frontal pose. In some cases, depth of features points on the left half of the face can be better estimated when the subject poses to expose the left half of the face and vice-versa.

Face mesh integration can include averaging one or more mesh data points. For example, integration can include averaging the (x,y) points. The normalized weights used in a weighted averaging can be identified as, for each pose p_i, {1<=i<=K}, where there are K poses: w_i=(1−abs(yaw_i)/(pi/2)). Total weights can be represented as $$W = \sum_{1}^{K} w_i = \text{w\_1} + \text{w\_2} + \ldots + \text{w\_K}.$$

Normalized weights can be represented as (u_1, u_2, . . . u_K)=(w_1/W, w_2/W, . . . w_K/W). In some cases, the (x,y) coordinate of the j'th feature point (1<=j<=N) can be averaged using the normalized weights.

Integration can include averaging the z points of a face mesh. For averaging the z points, weights on points on each side of the face can be computed separately. When the subject faces left, the weights computed can used to adjust the depth of feature points on the right and vice-versa. The weight can be computed as max(0, yaw/(pi/2)). Weights can be normalized following similar processes as described for (x,y) coordinates. In this way, z coordinate values can be refined using data from multiple different poses.

In some cases, the condition identifier engine 108 estimates a pose of a subject's head. For example, the condition identifier engine 108 can use a face mesh, generated from one or more obtained face images, to estimate a pose of a subject's head. In some cases, the condition identifier engine 108 can identify a search space for a front portion of an anterior cervical region using a height of a face mesh, e.g., either individually or with additional data, such as a tilt of the face mesh. For example, if a face is tilted slightly left and a face height is measured at 200 pixels, and a face width is measured at 150 pixels, then the condition identifier engine 108 can identify a search space for an anterior cervical region can be initialized as 150 pixels wide, 100 pixels in height, located below a face mesh with a same tilt as that of the face mesh. In some cases, identifying a search space can improve efficiency or accuracy of a detection of an anterior cervical region, e.g., by reducing a region within which to search for the anterior cervical region.

In some cases, the condition identifier engine 108 uses a face mesh to identify a vertical axis of a subject's face. For example, the condition identifier engine 108 can identify an axis that runs through the middle of a subject's face. The axis can split the face into two nearly symmetric halves. This axis can be referred to as a mid-facial axis.

In some cases, the condition identifier engine 108 performs an edge detection process. For example, within an identified search space for an anterior cervical region, the condition identifier engine 108 can perform an edge detection process. The condition identifier engine 108 can identify an anterior cervical region by detecting two nearly parallel lines—e.g., lines that are within a threshold level of being parallel. The condition identifier engine 108 can identify lines that represent a silhouette of an anterior cervical region in a front face pose, such as neck of a subject. The condition identifier engine 108 can use Hough transforms or other similar line fitting tools on edge imagery. The orientation of the mid-facial axis can be used as a starting point for a parameter search space, e.g., when invoking Hough transform or its equivalent algorithms for line fitting.

In some cases, the condition identifier engine 108 identifies a search space for an anterior cervical region using profile face images. A search space can be defined using a size or orientation of a face mesh, e.g., that is fit onto an image of a face taken in profile pose. The condition identifier engine 108 can perform an edge detector process within an identified search region and identify a region that captures elements of the anterior cervical region, such as a lower chin or neck.

In some cases, the condition identifier engine 108 identifies one or more facial elements. For example, the condition identifier engine 108 can identify a fiducial point, such as cricoid that corresponds to the adam's apple of a subject. A fiducial point can be estimated using a region of maximum gradient change from within a mid portion of an anterior cervical region. Menton can be identified as a highest point in a lower chin region below gnathion.

In some cases, the condition identifier engine 108 extracts one or more facial features. For example, the condition identifier engine 108 can extract data indicating a thyromental distance, thyromental angle, cricomental distance, or a combination of these, among others. The thyromental distance can correspond to a distance between the thyroid notch to a chin, e.g., when a head is extended. The thyromental distance can indicate a mandibular space. In general, the condition identifier engine 108 can identify aspects of Patil's Triangle which can include thyromental distance or thyromental line. Aspects of Patil's Triangle can indicate difficultly breathing—e.g., representing a risk factor for sleep apnea.

In some cases, the condition identifier engine 108 includes one or more deep learning models or shallower models (e.g., machine learning models). The one or more models of the condition identifier engine 108 can be trained to detect or characterize medical conditions, such as sleep apnea. The one or more models can characterize onset of medical conditions using single modal data or multi-modal data, such as the multi-modal 106 shown in the example of FIG. 1. Data processed by the condition identifier engine 108 can be gathered by the data capture engine 104. The data capture engine 104 can capture data using smartphone applications, sleep clinic data, or a combination of these, among others. One or more models of the condition identifier engine 108 can be trained in partial, or fully, supervised fashion.

Data types used for training can include data from a sleep questionnaire, a frontal face image, a sagittal face image, a voice sample (e.g., with or without restrictions to nasal passage), an image from within the oral cavity, or a combination of these among others. Ground truth data used for training can include data indicating a physician's diagnosis for a subject, where the training data includes corresponding input data for that subject. Ground truth data can include results from an overnight sleep test. Ground truth data can include an indication of whether or not a subject has a given medical condition, such as sleep apnea. Ground truth data can include an underlying cause identified by a physician in determining the given medical condition, e.g., if a subject had sleep apnea, then an underlying cause can include one or more of obesity, protruded jaw, enlarged tongue, crowded teeth, deviated septum, double chin, enlarged tonsils, or a combination of these among others. Ground truth data can include recommended interventions. For example, if a subject had sleep apnea, ground truth data can include what a medical professional recommended as an intervention, such as wearing a CPAP device, reduce BMI, mandibular advancement device, surgical procedures to trim uvula or tonsils, among others. The system 100 can collect ground truth data when available. The ground truth data can help build multi-tasking deep learning models, e.g., models that can perform operations, such as classifying a subject as one with a given medical condition, identifying one or more most likely causes of a condition, recommending interventions, or a combination of these among others.

Training and ground truth data can be specific to a medical condition to be identified. For example, ground truth data used for training to detect sleep apnea medical conditions can include data obtained using Apnea Hyponea Index (AHI) or a physician's diagnosis of mild apnea, moderate apnea, severe apnea, or no apnea. Ground truth data can include physician notes related to a subject, e.g., indicating obesity, high BMI, moderately high BMI, heart disease, previous medical issues, such as stroke, receded jaw, facial asymmetry, enlarged tonsils, enlarged tongue, crowded teeth, deviated septum, or a combination of these, among others. In some cases, the condition identifier engine 108 includes one or more language models trained to identify features from physician notes to be included in training data, e.g., as ground truth data.

In some cases, models of the condition identifier engine 108 output data indicating whether a subject presents conditions within a class of a plurality of severity classes. For example, a model can be trained to classify a subject as either belonging to or not belonging to one or more classes. The classes can include mild, moderate, severe, or no presence of a given medical condition, such as OSA. Ground truth data can include a classification for one or more training data subjects.

In some cases, one or more models of the condition identifier engine 108 are trained to attribute one or more elements of a subject's current biological state to a given identified medical condition. For example, a model can perform OSA attribution (e.g., identifying a likely cause(s) for sleep apnea based on evidence presented or data obtained) apart from, or in addition to, OSA classification. A model can, e.g., identify a subject's weight as a primary factor that is causing OSA or another medical condition identified by the condition identifier engine 108.

Example types of attributions can include one or more of the following: (i) Enlarged Neck circumference: attributing a medical condition to an enlarged neck circumference, e.g., when a subject gains weight; (ii) Facial retrusion: Can be characterized by a lack of forward projection of facial structures, including maxilla and mandible; (iii) Maxillo-mandibular insufficiency: Underdevelopment of both lower and upper jaw; (iv) Retrognathia: A retruded or posteriorly positioned lower jaw, which affects alignment of upper and lower teeth; (v) Micrognathia: An abnormally small jaw contributing to reduced airway space; (vi) Overbite: Excessive vertical overlap of the front teeth; (vii) Narrow nasal passages: Constriction in the nasal airways impeding airflow while breathing; (viii) Deviated septum: Differences in the size of the two nasal passages can lead to OSA; (ix) High arched palate: Affects the size and shape of the upper airway; (x) Enlarged tonsils or adenoids or long uvula: Physical obstructions to airway; (xi) Tired or fatigued appearance: Chronic sleep deprivation can lead to OSA; (xii) Periorbital Edema (Dark circles): Swelling around the eye can be indicative of sleep-disordered breathing, including sleep apnea. This can come from reduced oxygenation during sleep.

The example types of attributions provided specifically considers a medical condition of OSA but similar attributions could be generated, e.g., by the condition identifier engine 108, for other medical conditions. Other types of attributions not listed can be identified in some cases.

In some cases, the condition identifier engine 108 includes one or more trained models. Each of the one or more trained models can generate data that indicates the identified medical condition 110. For example, the one or more trained models can include a model that uses input from one or more sleep questionnaires. The input from the one or more sleep questionnaires can be mapped to a series of binary digits. With sufficient labeled data, the sleep questionnaire dataset can be fed as input to a model, such as a multilayer perceptron or multilabel support vector machine. The model can include a lightweight medical condition classifier, such as an OSA classifier.

In some cases, the one or more trained models includes a model using input data from one or more time-series inputs—e.g., a subject's wearable device data streams. The input data can indicate sleep quality, pulse rate, blood glucose level, physical exercise, bodily composition (BMI related), or a combination of these among others. The input data can be gathered over a period of time. The model can be configured for time-series data. The model can be a deep learning model that is trained to obtain data, such as data from one or more time-series inputs, and provide an indication of a medical condition.

In some cases, the one or more trained models includes a model using input data representing frontal or sagittal views of a subject's face. For example, both raw face images and one or more vertices of a face mesh can be provided to the model, which can include deep learning architecture. The deep learning architecture can include a combination of one or more of: convolutional layers, convolutional blocks, skip connections, fully connected layers, activation functions, or pooling layers. The loss functions can be configured such that the deep learning system can perform both medical condition identification (e.g., OSA classification) and medical condition attribution (e.g., OSA attribution). Based on desired size and computational complexity of the model, the system 100 can use model quantization or model pruning techniques to build deep learning models that can run on the edge—e.g., on a device of the data capture engine 104.

In some cases, the one or more trained models includes a model using one or more voice samples from a subject. For example, the model can include one or more deep learning elements. The model can obtain two voice samples from a subject: one captured under usual settings and the other captured with restrictions to the nasal airway (such as nasal pinching). The model can be trained to identify differences in intonations from the two samples and, e.g., detect obstructions that exist in the nasal airway. In some cases, obstruction detections can be included in the identified medical condition 110.

In some cases, the one or more trained models includes a model that identifies if there are restrictions to an airway passage. For example, the model can obtain images from an oral cavity. Using the images, the model can identify if there are likely any restrictions to the airway passage. If restrictions are detected, the model can be configured to identify one or more factors that are attributed to the restrictions in the airway passage, such as (a) enlarged tonsils (b) enlarged tongue (c) high arched palate (d) crowded teeth, or a combination of these among others.

In some cases, the one or more trained models includes a model trained on multi-modal data, such as the multi-modal data 106. The multi-modal data can include one or more of text (e.g., a questionnaire), an image (e.g., frontal, sagittal views of the face and neck, or views from within the oral cavity), life-style data gathered from wearables, audio, or a combination of these among others. The model can be configured to perform medical condition classification or attribution or both.

In some cases, the one or more trained models includes a model trained to detect one or more medical conditions using extracted elements from images of a body. For example, the system 100 can obtain images of a subject's face. The images can include various representations of the subject's face. Angles and measurements of the subject's face can be extracted by the system 100 and used as input for a model to identify one or more medical conditions. In some cases, the system 100 extracts elements using a face mesh. Extracted elements, such as angles, aspect ratios, or other extracted data points from a subject's face, can be provided to the model in an N dimensional vector, where N represents the number of elements extracted from the one or more images of the subject. A support vector machine or random forest or similar such machine learning solution can be used to build a medical condition classifier or attributor model.

In some cases, the condition identifier engine 108 includes one or more trained models that include a deep learning architecture. In some cases, data is pre-processed by the data capture engine 104 and then provided as processed input to the condition identifier engine 108. In some cases, the condition identifier engine 108 performs pre-processing and processing or just processing, e.g., using one or more trained models. For example, a model can be based on a U-Net model for segmenting different anatomical regions in the oral cavity. This model can start with an input layer that processes high-resolution 2D or 3D scans of the oral cavity. An encoder path can include one or more convolutional layers with varying or increasing filter sizes, followed by Batch Normalization and ReLU activation. The encoder path can include max-pooling layers to capture contextual information by reducing spatial dimensions. At the bottleneck, dilated convolutions with larger receptive fields can be used to capture multi-scale context effectively. A decoder path can include upsampling layers using transposed convolutions or nearest-neighbor upsampling, followed by convolutional layers. Skip connections from the encoder to the corresponding decoder layers can help ensure recovery of spatial information lost during downsampling. A final output layer can use a SoftMax activation function, e.g., to classify each pixel into a respective anatomical region.

To enhance the model, attention mechanisms such as Attention U-Net can integrate attention gates in skip connections, e.g., to focus on relevant features and suppress background noise. Residual connections can facilitate training of deeper networks, while multi-scale features can capture details at various scales, e.g., through pyramid pooling or atrous spatial pyramid pooling (ASPP). A hybrid loss function combining Dice loss with cross-entropy loss can address class imbalance and help improve segmentation accuracy. The training process can incorporate data augmentation, transfer learning, and regularization techniques like dropout and weight decay to, e.g., ensure robust and precise segmentation of oral cavity anatomical regions.

Building on the segmentation maps generated by the U-Net model, the system 100 can use the maps for classification and medical condition detection, such as OSA. For example, specific metrics can be calculated from segmented regions, such as the size and volume of each anatomical structure, positional relationships, shape descriptors, and texture features. Functional features, like airway patency and dynamic changes in anatomical structures, can be assessed, e.g., if dynamic scans are available. The system 100 can include classification models using these metrics, e.g., to predict the onset of OSA. Feature selection techniques can identify the most relevant features, and classification models such as Support Vector Machines (SVMs), Random Forests, and Deep Learning models like CNNs or LSTMs can be trained. A training dataset can be split into training, validation, and testing sets, e.g., with k-fold cross-validation ensuring robustness and generalizability. Hyperparameter tuning can be performed using grid search or random search.

In some cases, the condition identifier engine 108 includes a segmentation model and a classification model. For example, the condition identifier engine 108 can process raw data, e.g., captured by the data capture engine 104, and generate maps using the segmentation model. The condition identifier engine 108 can extract features from the maps generated by the segmentation model. The condition identifier engine 108 can provide the extracted features to the classification model.

In some cases, a segmentation model can divide a face into various anatomical regions. Segmentation can be performed either in a learning-driven way or rule-based way. In learning driven way, the system 100 can provide ground truth labels for which face region corresponds to lower jaw, upper jaw, chin, mandible, maxilla, mouth, nose, nasal septum, among others. In a rule-based way, the system 100 can include rules that indicate, e.g., a face contour comprising a set of pre-defined indices form a lower jaw, certain other pre-defined indices form an upper jaw, and other indices can form other regions. In some cases, segmented features can help classification. For example, the condition identifier engine 108 can generate or obtain a segmented face and use that to identify conditions such as micrognathia, retrognathia, deviated septum, prognathic maxilla, or a combination of these, among others.

The condition identifier engine 108 can be evaluated using metrics, such as accuracy, precision, recall, F1 score, and AUC-ROC curve. Output of the condition identifier engine 108 can be clinically validated, e.g., by comparing predictions with polysomnography results or other results depending on the medical condition. The system 100 can be deployed in clinical settings or at home for real-time medical condition risk assessment, e.g., with continuous monitoring and updates to maintain and improve performance.

In some cases, the multi-modal data 106 indicates age related changes to a subject. For example, the multi-modal data 106 can include data across time, e.g., across one or more years. The condition identifier engine 108 can analyze changes across time to determine onset of a medical condition. The condition identifier engine 108 can obtain data of a frontal and side-view of the subject's face (e.g., one or more images). Images can be obtained, e.g., during a subject's annual physical exam. A face model in the form of a face mesh, e.g., comprising N vertices identified on the face, can be fit to the frontal and profile face images of the patient taken across years. The face models across time can be aligned with one another, e.g., using a midpoint of the eyes or other feature in the images. Changes between the images, e.g., captured by changes in face models, can be determined by the condition identifier engine 108. One or more trained models of the condition identifier engine 108 can use the changes to determine a presence of a medical condition. For example, the condition identifier engine 108 can identify physical drifts—e.g., in (X,Y,Z)—observed on different vertices (e.g., estimated on frontal faces and profile faces, respectively) across years. The physical drifts can be processed by a deep learning system to characterize sleep apnea onset.

The condition identifier engine 108 can include one or more trained models for determining an onset of a medical condition. For example, one or more models can be trained to detect one or more of the following signatures of OSA onset: (i) Rounding of face across years: Increase in facial fat deposits can result in puffy cheeks, rounded or swollen face. The increased fat deposits can be indicative of narrowed airways and hence higher likelihood of OSA; (ii) Appearance of double chin: Obesity, skin losing elasticity due to age, weakening of muscles due to age or lack of exercise, poor posture (slouching or frequently looking down on electronic devices) can result in double chin. This can increase a likelihood of OSA; (iii) Increased neck size: Neck circumference can be influenced by weight gain or loss. Excess weight gain can lead to increased fat deposits around the neck, potentially narrowing the airway and increasing likelihood of sleep apnea; (iv) Retrognathic Jaw position: Jaw position can directly impact the airway space. Tooth loss, dental treatments and natural aging factors can result in change in jaw position. Retruded lower jaw (mandible) can result in narrower airway space. (v) Chin projection: Loss in bone density and changes in facial soft tissue can result in reduced chin projection.

In some cases, the system 100 operates, at least in part, on an edge device. Sensitive data can be kept on a user device (e.g., of the data capture engine 104). For example, the condition identifier engine 108 can perform one or more processes, such as: (i) fitting face models to images obtained on an edge device; (ii) extracting features from a craniofacial complex of a subject; (iii) extracting features from an anterior cervical region, or a combination of these among others. The condition identifier engine 108 can be performed by a device on the edge, e.g., by a mobile device of a subject, such as a smartphone. In some cases, a face image can be discarded in response to features being extracted. The condition identifier engine 108 can save just the extracted features, e.g., fiducial feature locations, on an external memory device, e.g., on a server. By saving only the extracted features and not the original image of the subject, the sensitive data of the subject can be preserved with reduced risk of exposure. In some cases, the condition identifier engine 108 can save extracted features with data reference a corresponding location in one or more images obtained on a device of the data capture engine 104.

In some cases, the data capture engine 104 or the condition identifier engine 108 includes one or more encoders configured to encode data into one or more embeddings. The condition identifier engine 108 can include one or more transformers, e.g., that are data modality specific. The condition identifier engine 108 can include a cross-modal fusion transformer, e.g., that transformers output from the one or more transformers. The condition identifier engine 108 can use output of the cross-modal fusion transformer to generate the identified medical condition 110.

The multi-modal data 106 can include one or more of: (i) imagery taken from a subject's cervico-cranio-facial complex; (ii) subject's responses to a questionnaire; (iii) subject's voice samples with and without nasal airway restrictions, or a combination of these among others.

Images taken from the cervico-craniofacial complex can help characterize a subject's maxillomandibular morphology (mandibular insufficiency, retrognathia, micrognathia) and detect medical signatures, such as OSA signatures, such as hemifacial atrophy, submental fullness, periorbital hyperpigmentation, cervical hypertrophy. The sleep questionnaire can help characterize symptoms (such as gasping or choking during sleep, or loud snoring) that the subject may have witnessed along with their medical history, lifestyle, and functional impact of irregular sleep cycles. The voice samples can help characterize the subject's vocal expressions through their intonations and tonal quality, both indicative of potential obstructions to the nasal airway.

Deep learning neural networks, through multi-layered hierarchical structures, can be used on one or more data modes to process and provide analysis for subjects. Transformers can be used with input-embeddings, positional encoding mechanisms, self-attention, and cross-modal attention mechanisms. Sparsely gated mixture-of-experts layer can be used to integrate with transformer architectures to, e.g., increase a capacity of the model while keeping computational complexity of the model limited.

The system 100 can have one or more of the following components (e.g., as part of the data capture engine 104 or the condition identifier engine 108): (i) Input Embedding Engine: Each input modality can be pre-processed and converted to a respective embedding using pre-trained models such as ResNet or VGG or similar such for images, BERT or word2vec or similar such for text, Mel-frequency cepstral coefficients (MFCC) or similar such for audio; (ii) Modality-specific transformers: The embeddings obtained from each modality can be processed by transformers dedicated to process that modality. The transformer can comprise self-attention layers, residual layers, feedforward neural networks, and can extract complex patterns and interactions from within each modality; (iii) Fusion with cross-modal transformers: The output from modality-specific transformers can be concatenated and fed onto a cross-modal transformer that determines complex interactions across modalities. Cross-modal attention mechanism and positional encodings mechanism can be used; (iv) Sparsely gated Mixture-of-Experts layer: The architecture can include a set of experts (e.g., CNN-based, MLP-based, Transformer-based), one or more specialized at handling specific combinations of modalities. A gating network can be used to weigh the contributions of each expert based on input data; (v) Prediction head: A fully convolutional network or a fully connected layer can be deployed to aggregate information from the mixture of experts and produce a final sleep apnea detection result. In some cases, models used in the system 100 can be trained using unsupervised machine learning techniques, e.g., from video or images.

In some cases, one or more models of the system 100 are evaluated using test and validation datasets that are non-overlapping with training datasets. ROC-AUC curves, F1-scores, among other values can be generated to evaluate various operating points.

In some cases, the system 100 can be used to identify cardiovascular disease (CVD) either separately or in conjunction with OSA. For example, the data capture engine 104 can be configured to capture one or more of: (i) one or more images of a body part of the subject, such as a face or hand, or both a face and hand. Images can include images of front and back of both the left and right hand of a subject;

(ii) one or more images of subject's oral cavity; (iii) answers to questions, e.g., related to sleep or heart health.

The condition identifier engine 108 can be configured to perform one or more of: (i) face registration: Face image can be processed, e.g., by a pretrained deep learning model, to fit a model to the face. Model can identify over 100 feature points. A dense set of measurements can be extracted from the feature points (e.g., from the lower and upper jaw, from the lower face, from the mid face, or holistically); (ii) hand registration: A hand image can be processed, e.g., by a pretrained deep learning model, that identifies the finger joint locations; (iii) oral cavity registration: using an image processing library, the condition identifier engine 108 can detect teeth positions along a lower or upper jaw, correct for any in plane rotation, identify different components of the oral cavity pixel-wise, or perform a combination of these among other processes; (iv) converting questionnaire responses to a binary vector.

Ground truth data can be generated in the following way. A subject can visit a sleep clinic/cardiologist/general physician. The subject can provide data (e.g., face scan, hand scan, oral cavity scan, questionnaire answers, or a combination of these among others). The subject can be evaluated by a professional for a medical condition, such as OSA, CVD, or both among other conditions. A professional diagnosis (e.g., diagnostic code, visit summary, comorbid conditions, potential underlying conditions, suggested treatment plans) can be saved in Electronic Health Records. In some cases, over one thousand such records can be obtained. The records can indicate a mix of medical conditions, such as OSA only, CVD only, OSA and CVD, other conditions or condition combinations, or no conditions.

The condition identifier engine 108 can be configured to obtain one or more items of multi-modal data. The condition identifier engine 108 can include a transformer (e.g., based on a deep learning model). The transformer model can be trained for estimating a probability of a medical condition, such as a presence of OSA and CVD or one of these, among other conditions. The model can identify potential underlying causes. The model can recommend potential treatment plans.

Medical conditions identified by the system 100 can include Obstructive Sleep Apnea (OSA) with associated causes including retrognathic mandible, retrognathic maxilla, mandibular insufficiency, enlarged tonsils, enlarged adenoids, high arched palate, crowding of teeth, micrognathia, or a combination of these among others. The system 100 can detect one or more causes an attribute an identification of a medical condition to one or more of the causes.

Medical conditions identified by the system 100 can include CVD with associated causes including diagonal earlobe crease, xanthelasma, butterfly rash, Bells Palsy, xanthoma, arcus juvenilis, acanthosis nigricans, skin tags, ear lobe crease, nicotine stains, hyperpigmented hands in betel quid sellers, or a combination of these among others.

In some cases, the system 100 includes providing data to a medical professional for diagnosis. For example, the data capture engine 104 can capture data and provide at least a portion of the captured data to a medical professional. The medical professional can review the data provided. The medical professional can provide diagnostic information, such as a determined symptom or condition. In some cases, the medical professional can write a diagnosis. Information provided by the medical professional can be provided to the system 100, e.g., as part of the data capture engine 104. The information can be processed and used for determining one or more diagnoses. For example, a language model, such as a large language model, can parse text data from a medical professional to identify one or more factors or conditions within provided information. In some cases, the condition identifier engine 108 uses data extracted from information provided by a medical professional to help determine output results, e.g., the identified medical condition 110.

In some cases, a medical professional annotates captured data. For example, a medical professional can annotate one or more captured images to, e.g., identify a location of one or more regions in a mouth, such as teeth, tongue, uvula, tonsils, palate, or a combination of these among others.

Figure 2:
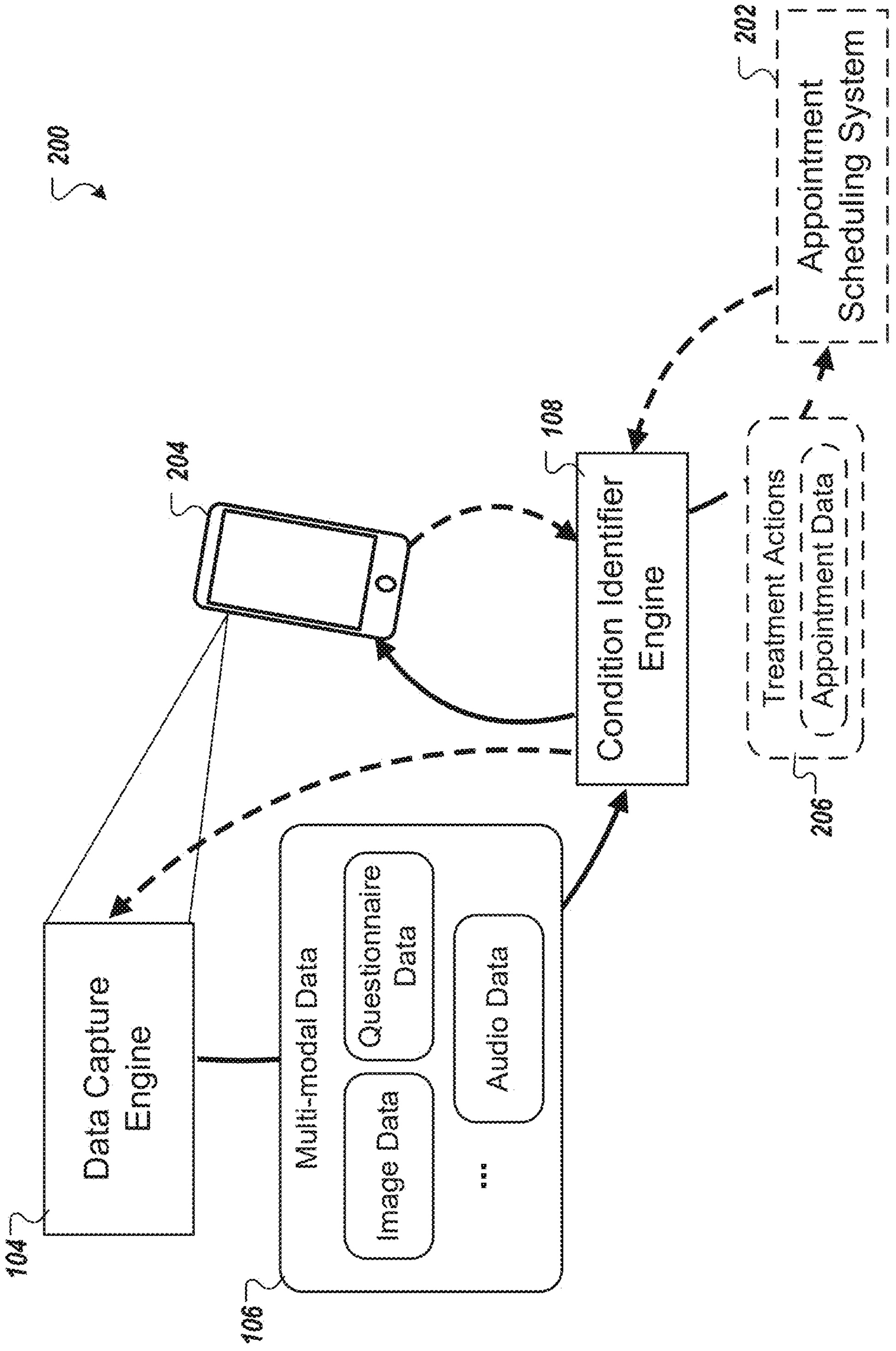
FIG. 2 shows another example medication condition determination system.

FIG. 2 shows another example medication condition determination system 200. The system 200 includes the data capture engine 104 and the condition identifier engine 108. The system 200 includes an appointment scheduling system 202 and a device 204 of the data capture engine 104. In some cases, the device 204 is a smartphone.

As described in reference to FIG. 1, the data capture engine 104 can obtain the multi-modal data 106 and provide the multi-modal data 106 to the condition identifier engine 108. In the example of FIG. 2, the condition identifier engine 108 includes one or more models trained to generate treatment actions 206. The treatment actions 206 can include appointment data. The condition identifier engine 108 provides the treatment actions 206 to the appointment scheduling system 202.

In some cases, the treatment actions 206 include an indication for scheduling an appointment. For example, if a likelihood of a medical condition satisfies one or more thresholds, the condition identifier engine 108 can generate one or more actions of the treatment actions 206 indicating an automatic appointment. The appointment scheduling system 202 can obtain an action indicating an automatic appointment and, in response, schedule an appointment for a given subject. The appointment scheduling system 202 can provide feedback data to the device 204, e.g., confirming a scheduled appointment, providing an interface to adjust a scheduled appointment, providing an interface to add the appointment to a device calendar, or a combination of these among others. In some cases, the appointment scheduling system 202 can access a subject's personal or work calendars, e.g., to identify an open time slot for scheduling an appointment. Appointment details can be provided by the appointment scheduling system 202 to a medical professional, e.g., providing indications of one or more medical condition risks, historical symptoms, or current symptoms.

In some cases, a severity, or likelihood of severity, of a given medical condition determined by the condition identifier engine 108 determines whether the condition identifier engine 108 generates treatment actions 206 that include an action (i) for automatic appointment scheduling, (ii) for optional appointment scheduling, or (iii) other health recommendations. In general, the condition identifier engine 108 can generate an action for automatic appointment scheduling in cases where a subject's medical condition poses a significant health risk, e.g., a risk of damage or harm to the subject's wellbeing in the near term. The condition identifier engine 108 can generate an action for optional appointment scheduling or other health recommendations—e.g., (i) manage a healthy weight, (ii) avoid alcohol or sedatives, (iii) avoid smoking, (iv) sleep on side, (v) establish regular sleep routine, or a combination of these among others—for medical conditions that are less severe, compared to medical conditions that cause the condition identifier engine 108 to generate an action for automatic appointment scheduling. In some cases, user preferences can determine what actions the condition identifier engine 108 generates, e.g., not automatically scheduling an appointment based on user preferences even if a medical condition would, for another user, be sufficient to cause the condition identifier engine 108 to generate an action for automatic scheduling.

In some cases, the system 100 or the system 200 can generate output that is transmitted to a medical system or to a user. For example, a system can create a diagnostic report, e.g., indicating output from the condition identifier engine 108. A report can be sent via email to a subject or medical professional. In some cases, a system can automatically upload data into an electronic medical record system or other application. Uploaded data can include output from the condition identifier engine 108. Uploaded data can be represented in various forms, such as PDFs, images, text, among others.

In some cases, the appointment scheduling system 202 provides information of a clinic or other medical professional to be visited by a subject. For example, the appointment scheduling system 202 can provide data indicating map directions to a medical professional, a building map for finding an office of a medical professional, a suggested time for leaving (e.g., based on predicted other scheduled appointments of the subject, traffic, among other factors), or a combination of these among others.

Figure 3:
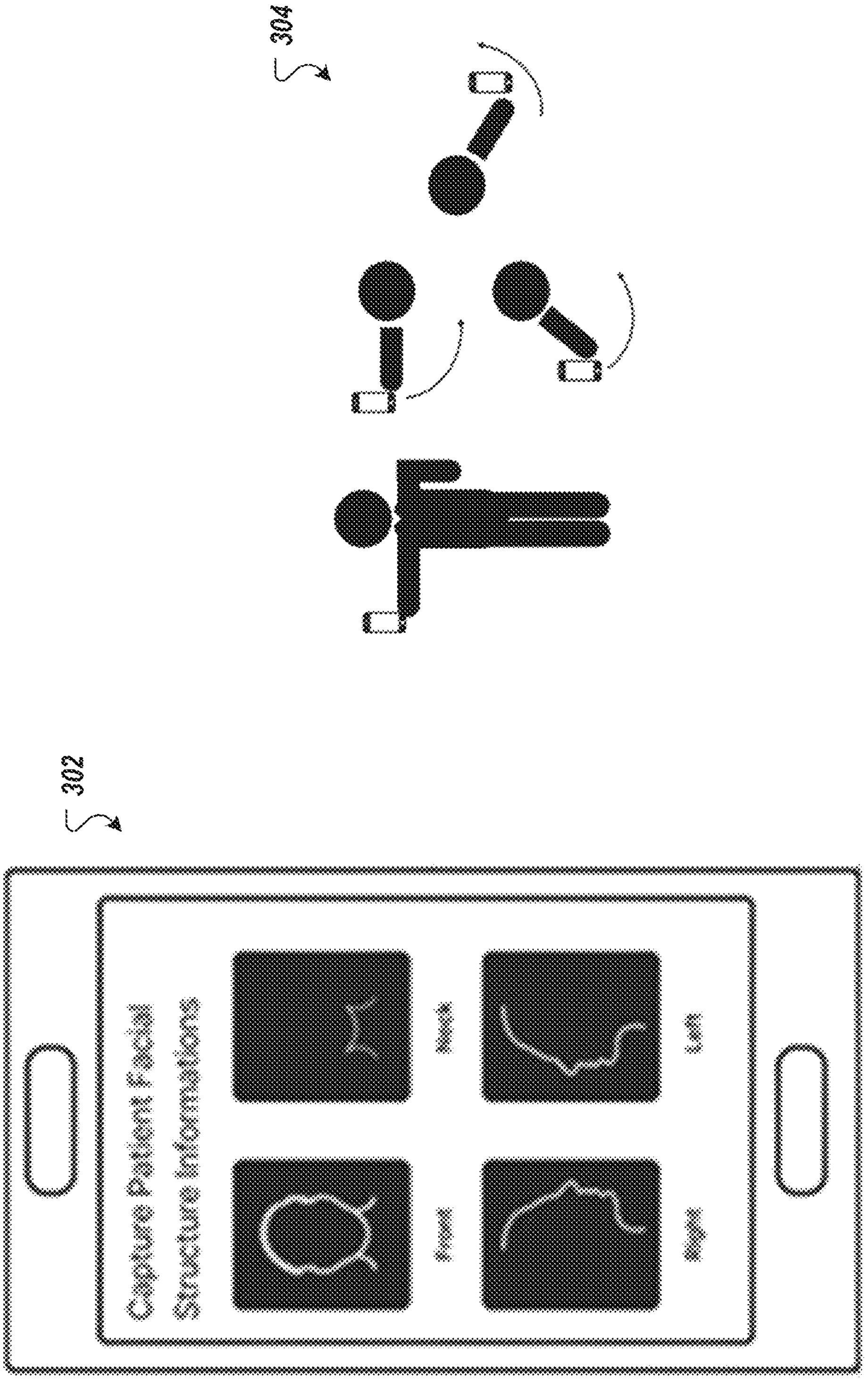
FIG. 3 shows example processes of data capture for a medication condition determination system.

FIG. 3 shows example processes of data capture for a medication condition determination system. A process 302 shows image capture using a device with a display, such as the device 204. The process 302 includes capturing one or more views of a subject's body. In this example, the process 302 shows capturing one or more views of a subject's face, including a front, neck, right, and left profile view. In some cases, the process 302 is performed by a device with a display and front facing camera, e.g., a smartphone. The process 302 can be performed, e.g., by the data capture engine 104. In some cases, the process 302 includes one or more audio or visual cues to a subject to display different views of body parts so that a camera can capture images of those body parts for processing. In some implementations, data capture using the process 302 is performed with assistance from a clinician (e.g., a doctor or other medical professional).

A process 304 shows a subject rotating a device, e.g., a device of the data capture engine 104, to obtain one or more views. For example, the process 304 can include obtaining one or more images, such as a single image or video. The process 304 can include a subject holding a device, such as a smartphone, and rotating the device around a body party of the subject to capture one or more views of the body part. In some cases, the different views captured can be used to generate a model of a body part, such as a face or other body part. The process 302 and 304 can be used to capture data for processing, e.g., by the system 100 to generate the identified medical condition 110 using one or more trained models of the condition identifier engine 108.

Figure 4:
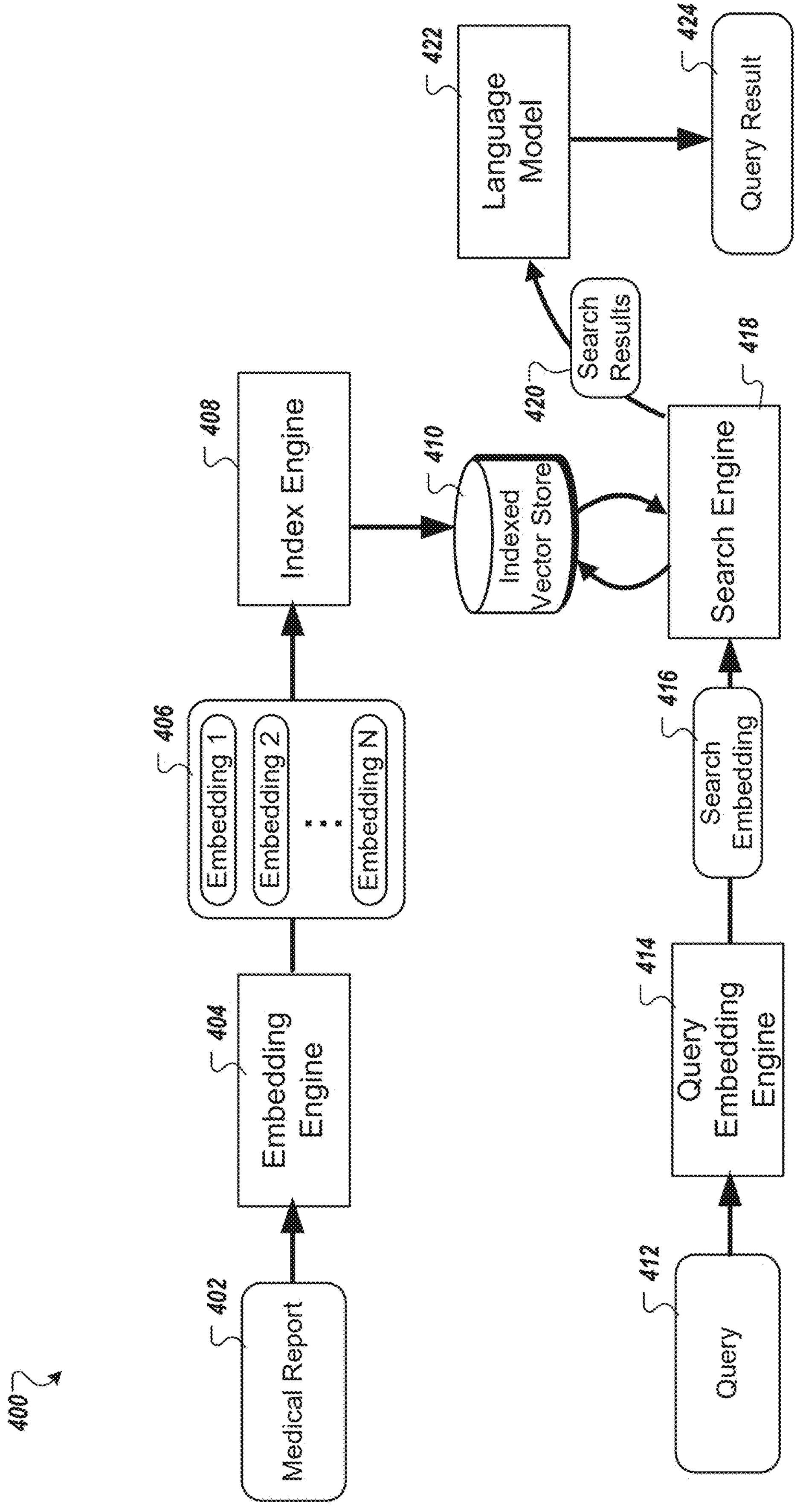
FIG. 4 shows an example system for processing medical reports.

FIG. 4 shows an example system 400 for processing medical reports. The system 400 includes an embedding engine 404, an index engine 408, an indexed vector store 410, a query embedding engine 414, a search engine 418, and a language model 422. In general, the system 400 processes one or more medical reports, such as medical report 402, and generates an indexed set of embeddings stored in the indexed vector store 410—e.g., within computer device memory. The system 400 can then query data in the indexed vector store 410 using a query 412. Search results 420 of the query can be provided to the language model 422. The language model 422 can use the search results 420 to generate a query result 424. In some cases, the query result 424 includes a written diagnosis or prediction of a medical condition for a subject.

In some cases, the embedding engine 404 obtains the medical report 402. The medical report 402 can be a report that is written by a medical professional, e.g., a doctor, and that indicates a medical condition of a subject. The embedding engine 404 can be configured to generate embeddings using the medical report 402 as input data. In some cases, the embedding engine 404 separates the medical report 402 into text chunks—e.g., words, phrases, sentences, paragraphs, or sections. The embedding engine 404 can then generate an embedding of the embeddings 406 for each of the separated text chunks. In some cases, the embedding engine 404 generates a set of embeddings without prior text separation. Text separation can be performed as a first part of a machine learning model that trained to generate embeddings or can be a separate process or machine learning model that is trained to separate text chunks of the medical report 402.

In some cases, non-text data is obtained from the medical report 402. The medical report 402 can include data from a medical record system. For example, the embedding engine 404 can embed one or more non-textual features included in the medical report 402. The non-textual features can include medical images, such as x-ray images, diagrams, or the like. In some cases, each non-textual element can be encoded by the embedding engine 404 as an embedding of the embeddings 406.

The embedding engine 404 can provide the embeddings 406 to the index engine 408. The index engine 408 can obtain the embeddings 406. The index engine 408 can use the embeddings 406 to generate one or more indexed embeddings which can be stored as indexed vectors in the indexed vector store 410. An indexing process can include mapping each vector to a specific position within a multidimensional space, e.g., using algorithms like k-d trees or locality-sensitive hashing (LSH). Indexing can allow for rapid similarity searches and enable quick and accurate retrieval of relevant information when querying an indexed data set.

The system 400 can include querying the data stored in the indexed vector store 410. For example, the query embedding engine 414 can obtain the query 412. The query 412 can include a query of a subject or medical professional, e.g., provided using a computer interface to one or more devices running the system 400, such as a desktop computer or smartphone. The query embedding engine 414 can generate a search embedding 416 using the query 412. For example, the query embedding engine 414 can generate an embedding similar to the embedding engine 404. An embedding can include one or more values that help to identify a given segment of text, such as a segment of the medical report 402 or at least a portion of the query 412.

The query embedding engine 414 can include one or more models that are trained to encode data into embeddings. For example, an embedding engine can be trained using an encoder and decoder network setup. An embedding engine can be an encoder. A system of an encoder and decoder and taken input data, such as text or non-text input. The encoder can transform the input into an embedding. The decoder can then attempt to generate the input data from the generated embedding. The decoder and encoder can be separately or jointly trained to generate an encoder and decoder pair that can generate embeddings sufficient to later generate the input data. After training, an encoder can be used in an embedding engine. Subsequent training can be performed as the system 400 performs operations, e.g., in response to an identified medical condition being determined to be correct or incorrect.

The query embedding engine 414 provides the search embedding 416 to a search engine 418. The search engine 418 can query the indexed vector store 410 to generate the search results 420. The search results 420 can indicate information related to the query 412, e.g., answers to one or more medical questions posed in the query 412. For example, the search results 420 can provide one or more historical medical conditions for subject A in response to the query 412 asking for one or more historical medical conditions for subject A.

In some cases, the language model 422 generates the query result 424 using one or more large language models. For example, the language model 422 can obtain the search results 420 and summarize the results as the query result 424. The query result 424 can be used, e.g., as output on a device for a user that provided the query 412 or as data for subsequent processes. For example, the query result 424 can be used for processing in the system 100. In the system 100, the data capture engine 104 can use the system 400 to obtain specific data for specific subjects, e.g., using historically obtained and processed medical reports.

In some cases, other data is processed by the system 400. For example, the system 400 can be configured to process non-medical report data. In general, the system 400 can process data that is related to a given subject. The data can then be stored for use in query results or to be used in further processing, e.g., to predict a presence of a medical condition, such as in the system 100 processes.

In some cases, the embedding engine 404 and the query embedding engine 414 include a pre-trained language model. In some cases, the embedding engine 404 and the query embedding engine 414 include the same embedding process, e.g., an embedding process of the language model 422. However, instead of generating output using solely the language model 422, the system 400 can use the search engine 418 to generate specific medical information to improve results from the language model 422. The language model 422 can use trained elements that simulate language understanding and context to interpret the search results 420.

Figure 5:
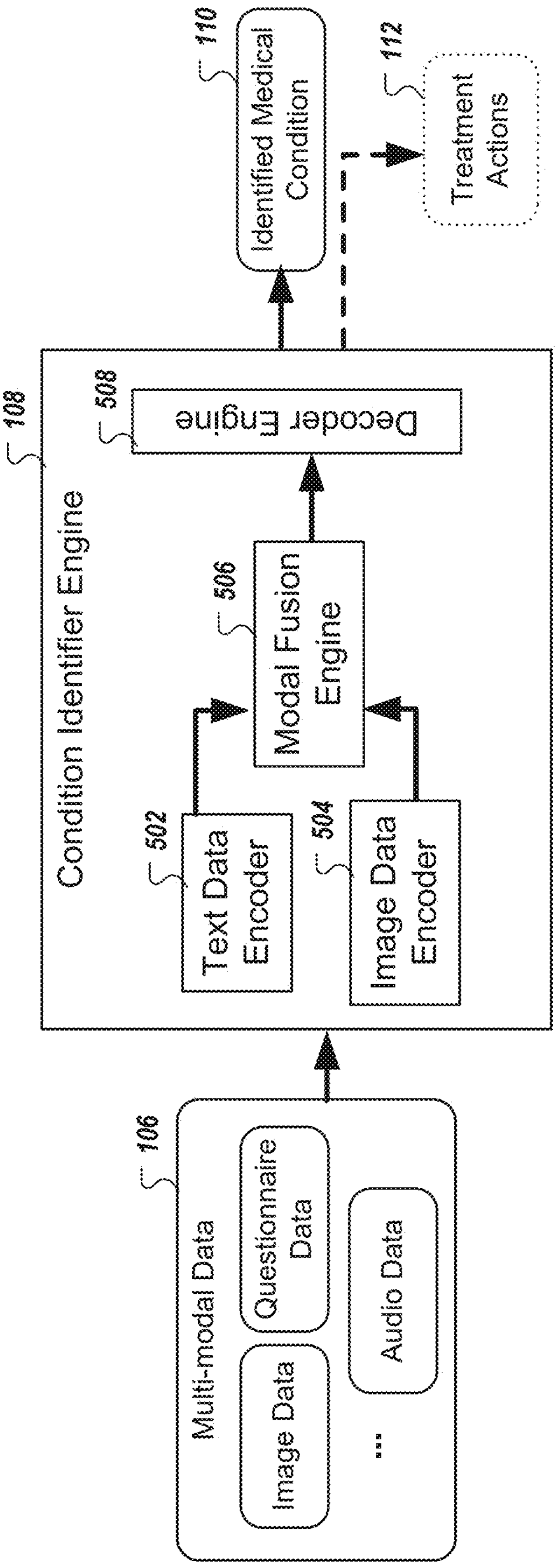
FIG. 5 shows additional elements of an example condition identifier engine.

FIG. 5 shows additional elements of an example condition identifier engine. For example, FIG. 5 shows additional details that can optionally be used in the system 100. In particular, FIG. 5 shows the condition identifier engine 108 with additional elements that include a text data encoder 502, an image data encoder 504, a modal fusion engine 506, and a decoder engine 508. In general, the condition identifier engine 108 can generate output that includes the identified medical condition 110 and the treatment actions 112.

In some cases, the text data encoder 502 generates one or more embeddings from text included in the multi-modal data 106, such as the questionnaire data. Embeddings can be generated in a similar manner to the embeddings shown and discussed in reference to the system 400 of FIG. 4. In some cases, the text data encoder 502 can obtain text data, e.g., from the questionnaire data or medical report data, and generate a vector of numbers. The vector of numbers can help to identify that data for downstream processing.

In some cases, the condition identifier engine 108 includes additional data encoders for other data modalities, such as the image data encoder 504. Although shown with only two encoders, the condition identifier engine 108 can include additional or fewer encoders in some cases. The image data encoder 504 can be configured to obtain image data, such as image data from the multi-modal data 106 that represents a body part of a subject, such as a face of the subject, and generate an embedding. The embedding can be a set of values that help to indicate a particular image or set of images.

In some cases, the modal fusion engine 506 fuses data from one or more encoders. For example, the modal fusion engine 506 can fuse data from the text data encoder 502 and the image data encoder 504. In some cases, the modal fusion engine 506 fuses data using one or more concatenation operations. For example, the modal fusion engine 506 can concatenate one or more embeddings, from one or more encoders, to generate a fused embedding to provide to the decoder engine 508. In some cases, the modal fusion engine 506 includes an encoder model, such as an encoder model that can be included in the text data encoder 502 and the image data encoder 504, that is configured to encode data from one or more encoders into a single output, such as a single embedding. The single embedding can be different from a concatenated embedding, e.g., it may be a compressed version of such a concatenated embedding or a new embedding, such as a new embedding that maps the obtained encoder data into a new feature space that is either the same or different dimension compared to the data from the one or more encoders.

In some cases, the decoder engine 508 obtains output data from the modal fusion engine 506. The decoder engine 508 can be configured to decode output data from the modal fusion engine 506 into outputs, such as one or more of the identified medical condition 110, the treatment actions 112, or a combination of these among others. The decoder engine 508 can be trained separately or jointly with one or more elements of the condition identifier engine 108. For example, the decoder engine 508 can obtain data from the modal fusion engine 506 indicating training input data, where the training input data corresponds to ground truth data indicating one or more outputs, such as an identified medical condition or treatment actions. The decoder engine 508 can generate estimated output. A system, such as the system 100 of FIG. 1, can generate a difference value indicating a difference between the estimated output of the decoder engine 508 and ground truth data. Based on the difference value, the system can update one or more weights or parameters of one or more models of the condition identifier engine 108. For example, the system can update one or more weights or parameters of one or more of the encoders, the modal fusion engine 506, the decoder engine 508, or a combination of these among others.

Figure 6:
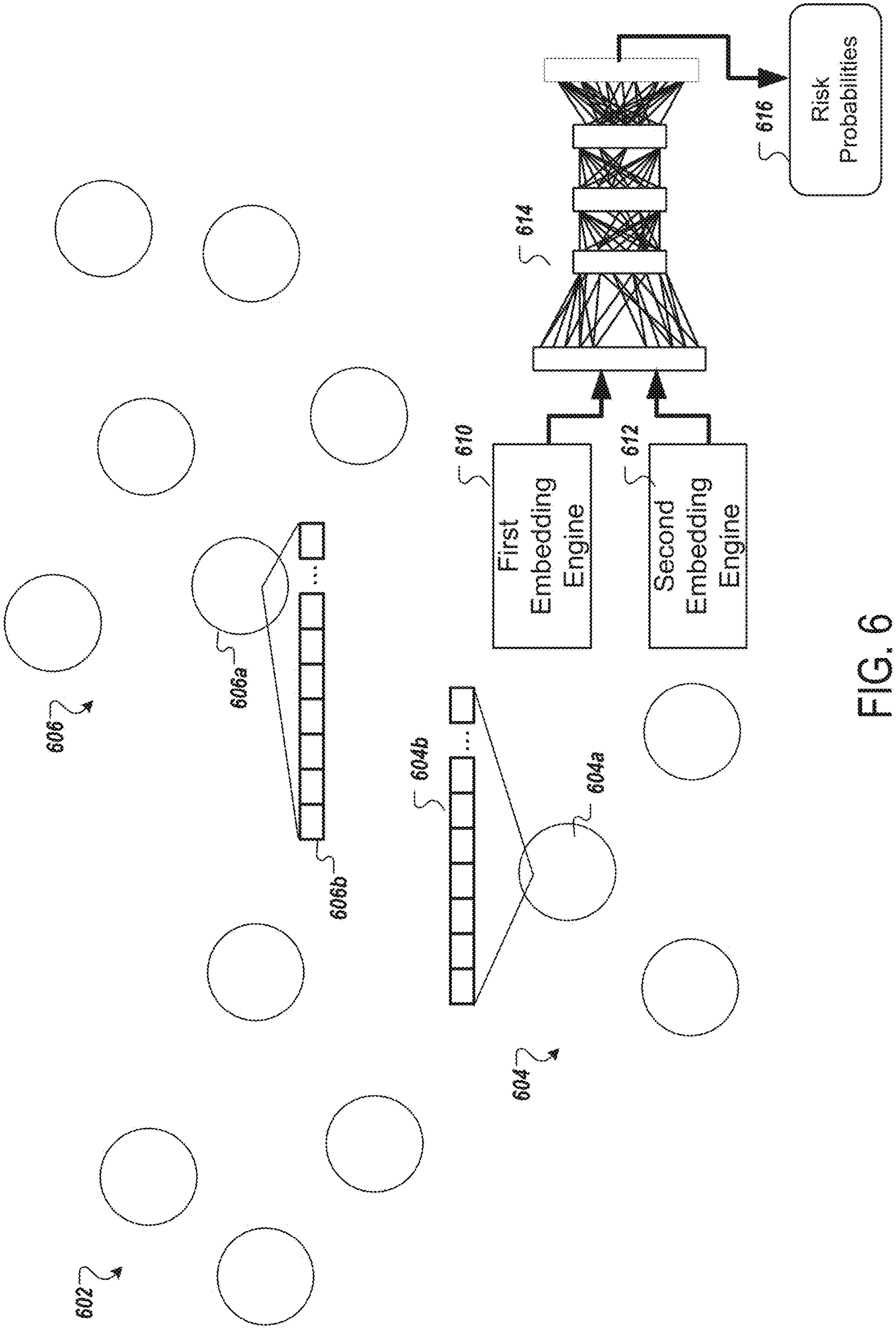
FIG. 6 shows an example subgraph process for risk probability predictions.

FIG. 6 shows an example subgraph process for risk probability predictions. FIG. 6 shows a collection of nodes representing subjects in a multi-dimensional space. For ease of illustration, the multi-dimensional space is depicted in two-dimensions. There are three clusters of nodes, including a first cluster 602, a second cluster 604, and a third cluster 606. Example nodes 604*a* and 606*a* are shown in the second and third clusters represented by the multi-dimensional vectors 604*b* and 606*b*, respectively. The multi-dimensional vectors can represent various features of different subjects.

In some cases, the nodes represent various features of different subjects, such as medical conditions, biographic information, ethnicity, or a combination of these among others. In general, nodes that are closer to one another represent subjects that are more medically similar to one another and nodes within the same cluster represent subjects that are more medically similar to one another than nodes representing subjects in different clusters.

In some cases, a first embedding engine 610 and a second embedding engine 612 can be used to generate output data using one or more values from the nodes. For example, the first embedding engine 610 and the second embedding engine 612 can be part of a subgraph neural network that serves as a multi-class classifier. In some cases, the subgraph neural network can identify comorbidity risks faced by ethnic minorities, the socioeconomically disadvantaged, subjects in underserved communities, or a combination of these among others.

In some cases, the first embedding engine 610 identifies feature embeddings using the nodes. For example, the first embedding engine 610 can identify feature embeddings on a holistic graph. In some cases, the embeddings can include values that represent a nodes position in a multi-dimensional space. The first embedding engine 610 can generate embeddings using data from one or more subjects. In some cases, the first embedding engine 610 is trained using a decoder to try and recreate input data based on an intermediate embedding generated by the first embedding engine 610 operating on input data.

In some cases, the second embedding engine 612 generates one or more embeddings using a more limited context compared to the first embedding engine 610. A more limited context can correspond to (a) similarity in ethnicity, age, or gender, (b) similarity in socio-economic status, (c) geographic proximity, among other similarities, e.g., indicated in a profile data. Where the first embedding engine 610 can generate an embedding for a given subject using a context of a multi-dimensional space that includes all subjects, the second embedding engine 612 can generate one or more embeddings using a context of a cluster, such as the first cluster 602. The second embedding engine 612 can be trained to generate embeddings, e.g., based on one or more first embeddings generated using the first embedding engine 610.

In some cases, embeddings from the first embedding engine 610 and the second embedding engine 612 are concatenated, e.g., by an operating system, such as the system 100. For example, embeddings from the first embedding engine 610 and the second embedding engine 612 can be concatenated and provided to machine learning model 614. In some cases, the machine learning model 614 includes a set of fully connected layers. In some cases, each layer can be followed by batch normalization layers and activation functions (ReLu). One or more layers can be provided to a softmax layer. Output of the softmax layer can include output indicating the risk probabilities 616. The risk probabilities 616 can indicate risk for one or more medical conditions for a subject, a group of subjects, a specific ethnic community, or a combination of these among others.

In some cases, each node in FIG. 6 represents a patient. Each node can include a numerical feature vector. A vector can include attributes like encoded zipcode, age, encoded gender, encoded ethnicity, income range, condition risk score, such as OSA risk score, or a combination of these, among others. Edges can be created based on similarity measures, such as geographic proximity or demographic similarity, with weights reflecting a strength of relationships between nodes. Ground truth labels or scores representing comorbidity risks can be assigned to each patient. This structured data, including one or more of node features, edge indices, edge weights, and ground truth, can be then combined into a data object for a graph neural network (GNN).

Comorbidity risk ground truth can be represented by one or more values, e.g., {100, 0, 50, 0, 0, 0} representing, respectively, {Heart disease, diabetes, hypertension, GERD, depression, Obesity}. A GNN can include layers such as Graph Convolution layers (GCN) and attention layers. Each layer can have their own initialized weights.

A GNN can compute a holistic and subgraph-based embeddings, e.g., through a series of propagation and aggregation steps. Initially, each node's feature vector can be updated by aggregating information from neighboring nodes, weighted by edge weights, using methods such as mean, sum, or max pooling, among others.

For one or more nodes, a holistic embedding can be identified that encompasses information from an expanded neighborhood. For one or more nodes, a subgraph-based embedding can be generated using a neighborhood of nodes (e.g., within a threshold distance in a vector space). A subgraph-based embedding can include identifying a node neighborhood to aggregate information, e.g., based data representing geographic regions or ethnic groups. A GNN can update node features within a subgraph context to produce localized embeddings.

In some cases, a combined holistic and subgraph embeddings can be used to predict comorbidity risks, e.g., by feeding them into a classifier, such as a multi-layer perceptron (MLP). The classifier can use these embeddings to learn complex patterns and relationships, e.g., between patient attributes and comorbidity risks.

During training, a model can minimize a loss function, such as cross-entropy loss, for classification tasks or mean squared error for regression tasks, through techniques such as backpropagation and weight updates. Once trained, a model can accurately predict comorbidity risks for new patients by leveraging a comprehensive and localized information captured in one or more embeddings. This can help enable healthcare providers to identify high-risk individuals and tailor interventions more effectively, ultimately improving patient outcomes and resource allocation.

Figure 7:
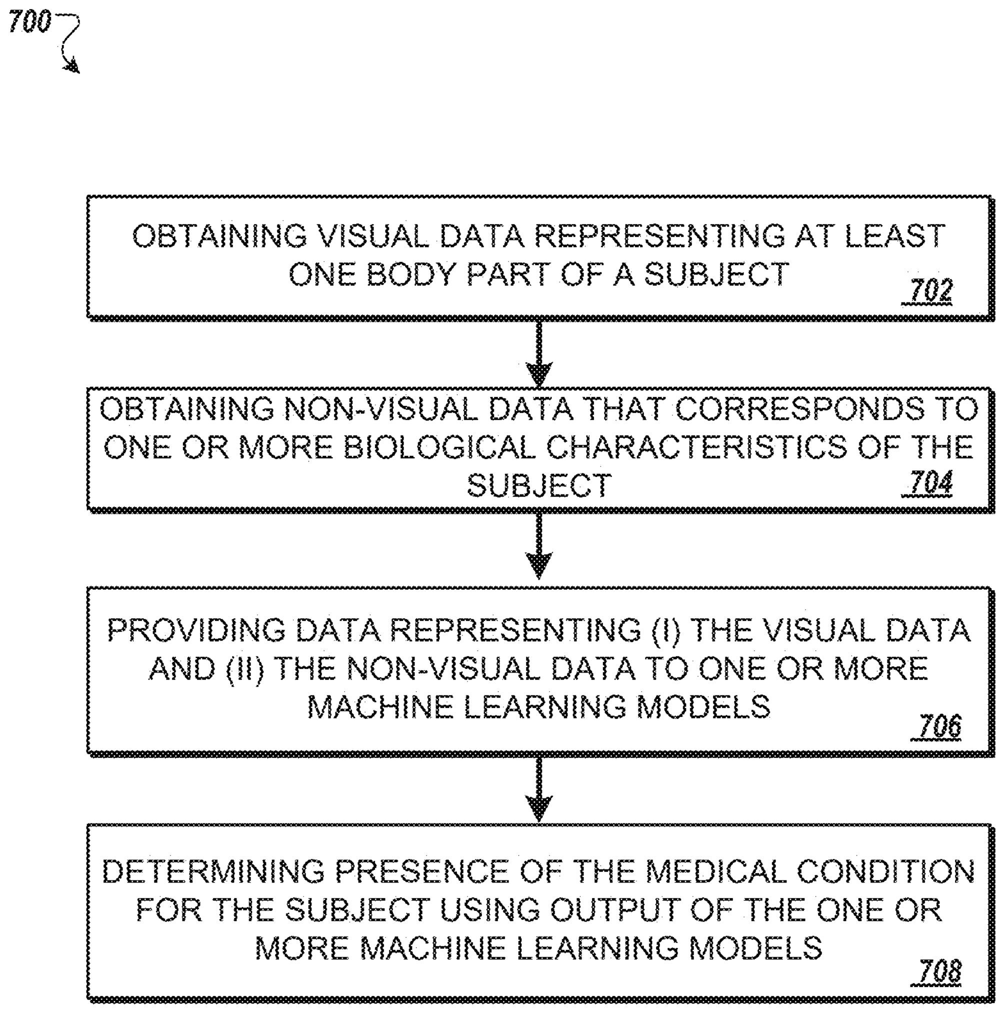
FIG. 7 is a flowchart of an example process for medical condition identification.

FIG. 7 is a flowchart of an example process 700 for medical condition identification. For convenience, the process 700 will be described as being performed by a system of one or more computers, located in one or more locations, and programmed appropriately in accordance with this specification. For example, a medical diagnostics system, e.g., the system 100 of FIG. 1, appropriately programmed, can perform the process 700.

The process 700 includes obtaining visual data representing at least one body part of a subject (702). For example, the data capture engine 104 of the system 100 can capture an image of a face of a subject.

The process 700 obtaining non-visual data that corresponds to one or more biological characteristics of the subject (704). For example, the data capture engine 104 of the system 100 can capture audio or questionnaire data to generate the multi-modal data 106.

The process 700 providing data representing (i) the visual data and (ii) the non-visual data to one or more machine learning models (706). The one or more machine learning models can be trained using a set of training data to predict presence of a medical condition. The one or more machine learning models can be included in the condition identifier engine 108 of the system 100.

The process 700 determining presence of the medical condition for the subject using output of the one or more machine learning models (708). The output of the one or more machine learning models can be generated based on the one or more machine learning models processing the visual data and the non-visual data. The condition identifier engine 108 can generate output including the identified medical condition 110. In some cases, the condition identifier engine 108 generates output including the treatment actions 112—e.g., for setting up an appointment or providing feedback to a subject or medical professional.

In some cases, output indicating a presence of the medical condition can be used for clinical decision support. For example, the system 100 can provide output to a medical profession to help the professional diagnosis one or more patients using data obtained for the one or more patients.

Figure 8:
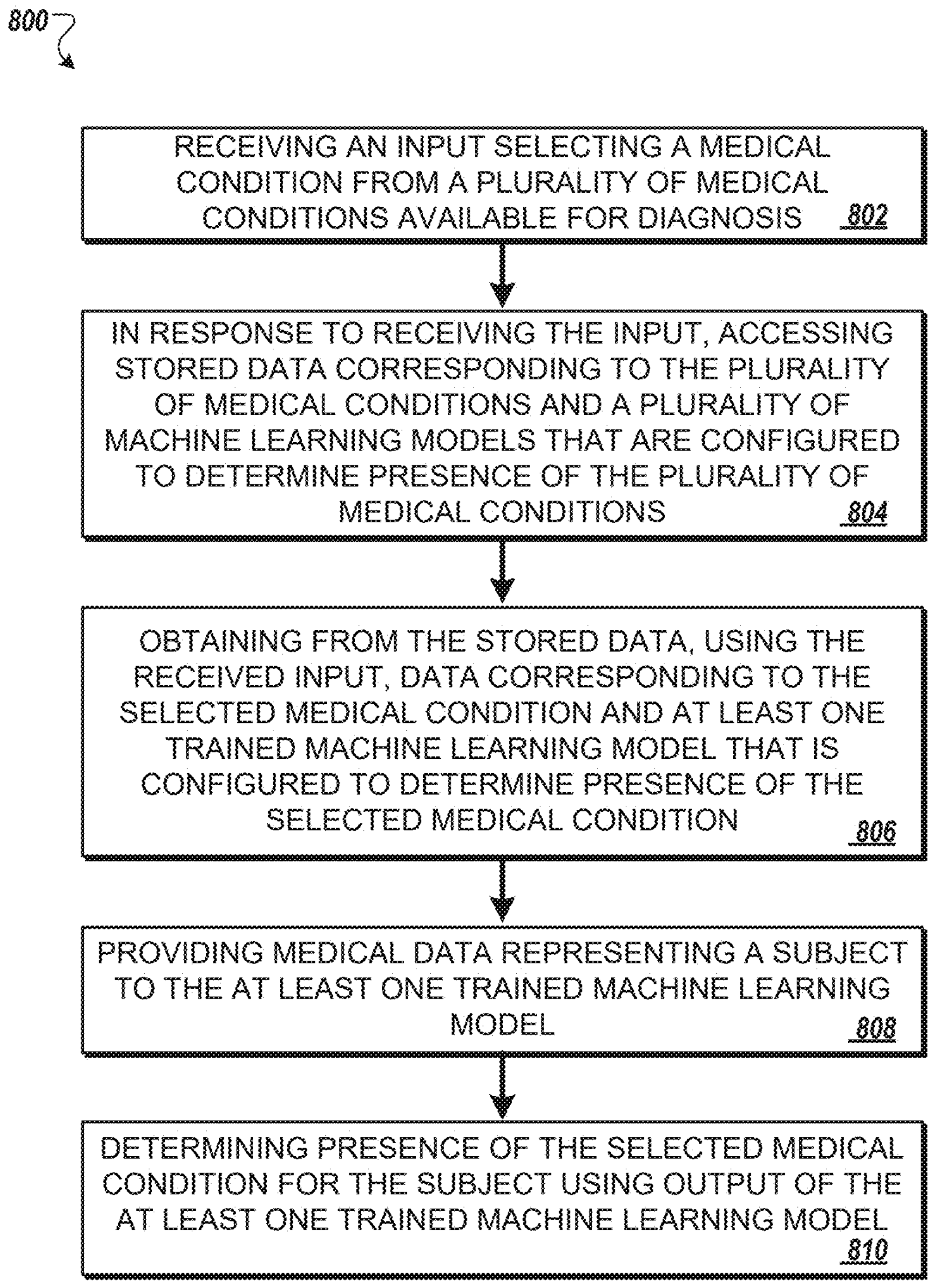
FIG. 8 is a flowchart of an example process for a medical condition identification platform.

FIG. 8 is a flowchart of an example process 800 for a medical condition identification platform. For convenience, the process 800 will be described as being performed by a system of one or more computers, located in one or more locations, and programmed appropriately in accordance with this specification. For example, a medical diagnostics system, e.g., the system 100 of FIG. 1, appropriately programmed, can perform the process 800.

The process 800 includes receiving an input selecting a medical condition from a plurality of medical conditions available for diagnosis (802). For example, a graphical user interface can be provided to allow a user to select from one or more available medication conditions. The user can be a subject for which a medical condition is to be identified for or a medical professional working to identify one or more medical conditions.

The process 800 includes, in response to receiving the input, accessing stored data corresponding to the plurality of medical conditions and a plurality of machine learning models that are configured to determine presence of the plurality of medical conditions (804). For example, a platform, such as one or more devices performing operations described in reference to FIG. 1, can store data corresponding to a plurality of medical conditions, such as OSA, heart disease, stroke, or other medical conditions. The platform can store a plurality of machine learning models that are configured to determine presence of the plurality of medical conditions. For example, in instances where the system 100 is configured to detect a presence of OSA, the system 100 can select elements of the condition identifier engine 108 based on the task of detecting the presence of OSA. In some cases, the system 100 stores a plurality of models, at least one of which is configured to detect a presence of OSA. The system 100 can configure the appropriate stored model for detection based on a detection selection by a user, e.g., configuring an OSA model in response to a user selecting OSA as a medical condition to be detected.

The process 800 includes obtaining from the stored data, using the received input, data corresponding to the selected medical condition and at least one trained machine learning model that is configured to determine presence of the selected medical condition (806). For example, a system, such as the system 100, can obtain data indicating a machine learning model. The data can include data for processing by the condition identifier engine 108, such as data of one or more models, such as data indicating parameter values, neural network layers, or a combination of these among others.

The process 800 includes providing medical data representing a subject to the at least one trained machine learning model (808). For example, a system, such as the system 100, can obtain data, e.g., using the data capture engine 104. Data captured can include medical data representing a subject. The data can be provided to a trained model, such as one or more trained models of the condition identifier engine 108.

The process 800 includes determining presence of the selected medical condition for the subject using output of the at least one trained machine learning model (810). In some cases, the output of the at least one trained machine learning model is generated based on the at least one trained machine learning model processing the medical data. For example, the condition identifier engine 108 can process data captured by the data capture engine 104 to generate the identified medical condition 110.

In some cases, the systems described include a continual learning based multimodal deep learning system. For example, the learning system can be designed for high capacity amidst conditional computations serving the purpose of medical condition screening, such as screening for OSA. When trained incrementally, e.g., in supervised fashion, on text-based and image-based subject records from multiple clinics, in the form of subject responses to sleep questionnaires and frontal images from subject's cervico-cranio-facial complex, a machine learning model of a system, such as the system 100, can be trained to determine intermodal correlations, preserve per-modal specificity, and develop an understanding of both symptomatic and anatomical signatures of obstructive sleep apnea.

Systems described, such as the system 100, can handle subtle variations to input data (which can be expected in datasets from across multiple clinics or data sources), for instance in the form of sleep questionnaires with subtle revisions to questions, images from the anterior cervical region, profile images of the cranio-facial complex, among others; (iii) One or more models of the system 100 can be trained to perform nuanced tasks such as treatment plans with incremental training and data annotations, e.g., from physician diagnostic codes.

Some traditional deep learning systems are monolithic and can suffer from catastrophic forgetting when tasked with incremental learning. Further, some systems face dense activations and hence high-capacity systems can typically suffer from computational bottlenecks. The techniques described can help avoid these limitations. For example, techniques can include using systems with deep learning architecture and one or more transformers. Transformers can be modality agnostic and include multi-head self-attention mechanism that efficiently captures dependencies and relationships within input data. A system can include one or more expert layers, e.g., that sit atop transformer encoder blocks, that leverage expertise of one or more specialized sub-models to handle different aspects of input data. Expert models can themselves be separate transformers or CNNs or ResNets. A system can include an application of softmax or sigmoid-based gating mechanisms that assign weights to individual expert models and perform expert fusion. The fused output can be provided to subsequent layers to generate a final output. A system can be trained using one or more loss functions.

In some cases, data, such as heterogenous data, is preprocessed. For example, processes performed by described systems, such as the system 100, can include tokenization and data embedding strategies for text and image-based input data streams, e.g., obtained from multiple clinics. Techniques can include data augmentation, data alignment, synchronization, or a combination of these among others. A system can generate standardized ground-truth labels, e.g., using one or more physician diagnostic codes.

In some cases, train, test, or validation data sets are identified. For example, non-overlapping data sets that are representative of real-world scenarios can be identified for use in training, testing, or validation. In some cases, data sets that are representative of real-world scenarios can be included in training data sets and data sets with missing data or noisy data can be included in the test and validation data sets.

In some cases, techniques include regression testing. For example, as a de-risking strategy, techniques can include iteratively validating performance and generalization of the system using representative datasets. Techniques can include identifying potential biases, overfitting, model complexity, or a combination of these among others. A system can include hyperparameter tuning, e.g., by deploying a cluster of servers to obtain an initial operating point.

The described techniques allow for screening large populations for medical conditions such as Obstructive Sleep Apnea (OSA) or other conditions. The described techniques allow for creating Clinical Decision Support (CDS) reports that help expedite physician's review of a patient. The CDS report can include output from a subject screening and can provide supplementary information in the form of recommended interventions or comorbid risk conditions the subject may be exposed to given their age, gender, ethnic background, or other factors. The described techniques allow for developing deep learning models that cater to specific populations. Techniques can include data capture using a smartphone with a camera and internet connectivity. Techniques can be performed as a part of a remote telehealth visit.

Techniques can help make screen or diagnosis for medical conditions, such as sleep apnea, accessible, especially for people far from existing diagnosis or screening professionals. The techniques can enable personalized screening or diagnosis that can help with early detection of medical conditions, e.g., by combining subjective user reported data with objective biological data, such as images obtained of a subject. Techniques can include providing a personalized recommendation to medical professionals with decision support on optimal treatment, such as oral appliance therapy through a dentist or sleep dentist, CPAP therapy, prescription medication, lifestyle changes, surgical intervention, e.g., stimulation or mandibular advancement, or a combination of these among others.

The subject matter and the actions and operations described in this specification can be implemented in digital electronic circuitry, in tangibly-embodied computer software or firmware, in computer hardware, including the structures disclosed in this specification and their structural equivalents, or in combinations of one or more of them. The subject matter and the actions and operations described in this specification can be implemented as or in one or more computer programs, e.g., one or more modules of computer program instructions, encoded on a computer program carrier, for execution by, or to control the operation of, data processing apparatus. The carrier can be a tangible non-transitory computer storage medium. Alternatively or in addition, the carrier can be an artificially-generated propagated signal, e.g., a machine-generated electrical, optical, or electromagnetic signal, that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

The term "data processing apparatus" encompasses all kinds of apparatus, devices, and machines for processing data, including by way of example a programmable processor, a computer, or multiple processors or computers. Data processing apparatus can include special-purpose logic circuitry, e.g., an FPGA (field programmable gate array), an ASIC (application-specific integrated circuit), or a GPU (graphics processing unit). The apparatus can also include, in addition to hardware, code that creates an execution environment for computer programs, e.g., code that constitutes processor firmware, a protocol stack, a database management system, an operating system, or a combination of one or more of them.

A computer program can be written in any form of programming language, including compiled or interpreted languages, or declarative or procedural languages; and it can be deployed in any form, including as a stand-alone program, e.g., as an app, or as a module, component, engine, subroutine, or other unit suitable for executing in a computing environment, which environment may include one or more computers interconnected by a data communication network in one or more locations.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

A computer program may, but need not, correspond to a file in a file system. A computer program can be stored in a portion of a file that holds other programs or data, e.g., one or more scripts stored in a markup language document, in a single file dedicated to the program in question, or in multiple coordinated files, e.g., files that store one or more modules, sub-programs, or portions of code.

The processes and logic flows described in this specification can be performed by one or more computers executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or both, or any other kind of central processing unit. Generally, a central processing unit will receive instructions and data from a read-only memory or a random access memory or both. The essential elements of a computer are a central processing unit for executing instructions and one or more memory devices for storing instructions and data. The central processing unit and the memory can be supplemented by, or incorporated in, special-purpose logic circuitry.

Generally, a computer will also include, or be operatively coupled to, one or more mass storage devices, and be configured to receive data from or transfer data to the mass storage devices. The mass storage devices can be, for example, magnetic, magneto-optical, or optical disks, or solid state drives. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

To provide for interaction with a user, the subject matter described in this specification can be implemented on one or more computers having, or configured to communicate with, a display device, e.g., a LCD (liquid crystal display) monitor, or a virtual-reality (VR) or augmented-reality (AR)

display, for displaying information to the user, and an input device by which the user can provide input to the computer, e.g., a keyboard and a pointing device, e.g., a mouse, a trackball or touchpad. Other kinds of devices can be used to provide for interaction with a user as well; for example, feedback and responses provided to the user can be any form of sensory feedback, e.g., visual, auditory, speech, or tactile feedback or responses; and input from the user can be received in any form, including acoustic, speech, tactile, or eye tracking input, including touch motion or gestures, or kinetic motion or gestures or orientation motion or gestures. In addition, a computer can interact with a user by sending documents to and receiving documents from a device that is used by the user; for example, by sending web pages to a web browser on a user's device in response to requests received from the web browser, or by interacting with an app running on a user device, e.g., a smartphone or electronic tablet. Also, a computer can interact with a user by sending text messages or other forms of message to a personal device, e.g., a smartphone that is running a messaging application, and receiving responsive messages from the user in return.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform the operations or actions. That one or more computer programs is configured to perform particular operations or actions means that the one or more programs include instructions that, when executed by data processing apparatus, cause the apparatus to perform the operations or actions. That special-purpose logic circuitry is configured to perform particular operations or actions means that the circuitry has electronic logic that performs the operations or actions.

The subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some implementations, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In some implementations, the computing system can operate in "privacy preserving mode" or offline mode, e.g., where processing or analysis is done on a client side or inside other devices. A trained model and system libraries can be packaged as a SDK and embedded in an application on a client side to do partial (such as biometrics or other processing) or complete processing on the edge.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Similarly, while operations are depicted in the drawings and recited in the claims in a particular order, this by itself should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:

accessing at least one of (i) first visual data representing a frontal view of a head of a subject, (ii) second visual data representing a side view of the head of the subject, or (iii) third visual data representing an upward looking view of the head of the subject;

fitting a three-dimensional face mesh comprising a plurality of vertices, each vertex of the plurality of vertices associated with three-dimensional coordinates, to at least one of (i) the first visual data, (ii) the second visual data, or (iii) the third visual data;

computing, using the three-dimensional face mesh, an estimated pose of the head of the subject, wherein the estimated pose comprises at least one of a roll angle, a pitch angle, or a yaw angle of the head;

identifying, using the three-dimensional face mesh and the estimated pose of the head of the subject, a search region corresponding to at least one of a craniofacial region or an anterior cervical region of the head of the subject;

determining, from within the search region, a plurality of quantitative measurements of at least one of the craniofacial region or the anterior cervical region, wherein the plurality of quantitative measurements are determined from anatomical landmarks localized within the search region based on the estimated pose and geometric relationships specified by the three-dimensional face mesh;

generating, using at least the plurality of quantitative measurements, an N-dimensional vector, wherein N represents a number of the quantitative measurements;

providing the N-dimensional vector as input to a machine learning model that is trained, using at least one of craniofacial region or anterior cervical region measurements from a plurality of training subjects having known sleep apnea diagnoses, to identify a sleep apnea condition;

obtaining, as an output of the machine learning model, a likelihood of the sleep apnea condition of the subject, wherein the likelihood of the sleep apnea condition is generated by the machine learning model based on processing the N-dimensional vector generated using at least the plurality of quantitative measurements provided as input to the machine learning model;

in response to obtaining the output of the machine learning model indicating that the likelihood of the sleep apnea condition satisfies a threshold, generating attribution data identifying one or more anatomical features of the subject attributed as underlying causes of the sleep apnea condition, wherein the one or more anatomical features are selected from at least one of retrognathia, micrognathia, maxillomandibular insufficiency, enlarged neck circumference, or facial retrusion; and transmitting, to an electronic device, a signal comprising information corresponding to the likelihood of the sleep apnea condition of the subject, wherein the signal is configured to display information representing a potential sleep apnea condition of the subject and recommendation data for at least one therapeutic intervention selected based on the attribution data.

2. The method of claim 1, wherein providing the N-dimensional vector to the machine learning model comprises:

providing at least one of an angle or aspect ratio representing the head of the subject to the machine learning model trained to identify the sleep apnea condition.

3. The method of claim 1, wherein accessing the second visual data representing the side view of the head of the subject comprises:

accessing visual data corresponding to a profile view of the head of the subject.

4. The method of claim 1, wherein fitting the three-dimensional face mesh to at least one of (i) the first visual data, (ii) the second visual data, or (iii) the third visual data comprises:

fitting a plurality of three-dimensional face meshes to at least one of (i) the first visual data, (ii) the second visual data, and (iii) the third visual data, wherein each three-dimensional face mesh comprises a plurality of vertices, each vertex being associated with three-dimensional coordinates;

computing, using the plurality of three-dimensional face meshes, respective estimated poses of the head of the subject, wherein each estimated pose comprises at least one of a roll angle, a pitch angle, or a yaw angle of the head;

integrating the plurality of three-dimensional face meshes to generate an integrated three-dimensional face mesh by computing weighted averages of vertex coordinates using normalized weights derived from the respective estimated poses;

computing, using the integrated three-dimensional face mesh, a final estimated pose of the head of the subject; and identifying, using the integrated three-dimensional face mesh and the final estimated pose, the search region.

5. The method of claim 1, wherein the plurality of quantitative measurements are associated with at least one of: to a neck of the subject, submental fullness of the neck of the subject, forward head posture, enlarged neck, adenoid facies, long face, facial swelling, face roundedness, lip incompetence, ptosis, eye bags, receding jaw, malocclusion, facial retrusion, maxillomandibular insufficiency, retrognathia, micrognathia, overbite, narrow nasal passages, deviated septum, tired or fatigued appearance, or periorbital edema.

6. The method of claim 1, further comprising accessing non-visual data that corresponds to one or more biological characteristics of the subject, wherein providing the N-dimensional vector as input to the machine learning model comprises:

providing N-dimensional vector to a first type of machine learning model; and providing information representing the non-visual data to a second type of machine learning model.

7. The method of claim 6, wherein providing the N-dimensional vector to the first type of machine learning model comprises:

providing the N-dimensional vector to a convolutional neural network (CNN), wherein providing the information representing the non-visual data to the second type of machine learning model comprises:

providing the information representing the non-visual data to a recurrent neural network (RNN).

8. The method of claim 6, further comprising:

providing (i) output from the first type of machine learning model and (ii) output from the second type of machine learning model to a decoder model that is trained to identify the sleep apnea condition using outputs from the first and second types of machine learning models, wherein obtaining, as the output of the machine learning model, the likelihood of the sleep apnea condition of the subject comprises:

obtaining an output of the decoder model that indicates the likelihood of the sleep apnea condition of the subject.

9. The method of claim 6, further comprising:

generating a first embedding representing at least a portion of (i) the first visual data, (ii) the second visual data, and (iii) the third visual data;

generating a second embedding representing at least a portion of the non-visual data; and generating a fused data set that combines the first embedding and the second embedding, wherein providing the N-dimensional vector as input to machine learning model that is trained to identify the sleep apnea condition comprises providing the fused data set to the machine learning model, and wherein the output of the machine learning model is based on processing of the fused data set by the machine learning model.

10. The method of claim 1, further comprising:
accessing data representing an oral cavity of the subject, the data comprising representation of at least one of lower teeth, upper teeth, habitual occlusion, tongue, upper palette, or oropharyngeal region; and
determining, using the data representing the oral cavity of the subject, at least one of a high arched palate, enlarged tonsils, adenoids or long uvula, scalloped tongue, macroglossia, malocclusion, overbite, underbite, crossbite, crowding, gapped teeth, open bite, overjet, abnormal eruption, a Mallampati class, or bruxism,
wherein the information indicating at least one of a high arched palate, enlarged tonsils, adenoids or long uvula, scalloped tongue, macroglossia, malocclusion, overbite, underbite, crossbite, crowding, gapped teeth, open bite, overjet, abnormal eruption, a Mallampati class, or bruxism is additionally provided as input to the machine learning model.

11. The method of claim 1, wherein computing the estimated pose of the head of the subject using the three-dimensional face mesh comprises:
providing the three-dimensional face mesh to a second machine learning model that is trained to estimate a pose of a subject head or a rule-based engine that estimates a head pose.

12. The method of claim 1, wherein identifying the search region comprises:
identifying, using the three-dimensional face mesh, a mid-facial axis that divides a craniofacial region of the subject into two substantially symmetric halves; and
using an orientation of the mid-facial axis to define a parameter for a line-fitting process performed within the search region.

13. The method of claim 1, wherein the machine learning model is further trained using a training library comprising labeled ground truth images that represent silhouettes in an anterior cervical region and fiducial features corresponding to menton and cricoid elements in the anterior cervical region of the training subjects.

14. The method of claim 1, wherein the plurality of quantitative measurements comprises at least one of a thyromental distance, a thyromental angle, or a cricomental distance.

15. The method of claim 1, further comprising:
determining an estimated three-dimensional profile of the head of the subject; and
generating the N-dimensional vector using the estimated three-dimensional profile in conjunction with the plurality of quantitative measurements.

16. A system comprising:
one or more computers and one or more storage devices on which are stored instructions that are operable, when executed by the one or more computers, to cause the one or more computers to perform operations comprising:
accessing at least one of (i) first visual data representing a frontal view of a head of a subject, (ii) second visual data representing a side view of the head of the subject, or (iii) third visual data representing an upward looking view of the head of the subject;
fitting a three-dimensional face mesh comprising a plurality of vertices, each vertex of the plurality of vertices associated with three-dimensional coordinates, to at least one of (i) the first visual data, (ii) the second visual data, or (iii) the third visual data;
computing, using the three-dimensional face mesh, an estimated pose of the head of the subject, wherein the estimated pose comprises at least one of a roll angle, a pitch angle, or a yaw angle of the head;
identifying, using the three-dimensional face mesh and the estimated pose of the head of the subject, a search region corresponding to at least one of a craniofacial region or an anterior cervical region of the head of the subject;
determining, from within the search region, a plurality of quantitative measurements of at least one of the craniofacial region or the anterior cervical region, wherein the plurality of quantitative measurements are determined from anatomical landmarks localized within the search region based on the estimated pose and geometric relationships specified by the three-dimensional face mesh;
generating, using at least the plurality of quantitative measurements, an N-dimensional vector, wherein N represents a number of the quantitative measurements;
providing the N-dimensional vector as input to a machine learning model that is trained, using at least one of craniofacial region or anterior cervical region measurements from a plurality of training subjects having known sleep apnea diagnoses, to identify a sleep apnea condition;
obtaining, as an output of the machine learning model, a likelihood of the sleep apnea condition of the subject, wherein the likelihood of the sleep apnea condition is generated by the machine learning model based on processing the N-dimensional vector generated using at least the plurality of quantitative measurements provided as input to the machine learning model;
in response to obtaining the output of the machine learning model indicating that the likelihood of the sleep apnea condition satisfies a threshold, generating attribution data identifying one or more anatomical features of the subject attributed as underlying causes of the sleep apnea condition, wherein the one or more anatomical features are selected from at least one of retrognathia, micrognathia, maxillomandibular insufficiency, enlarged neck circumference, or facial retrusion; and
transmitting, to an electronic device, a signal comprising information corresponding to the likelihood of the sleep apnea condition of the subject, wherein the signal is configured to display information representing a potential sleep apnea condition of the subject and recommendation data for at least one therapeutic intervention selected based on the attribution data.

17. The system of claim 16, wherein the plurality of quantitative measurements are associated with at least one of: a neck of the subject, submental fullness of the neck of the subject, forward head posture, enlarged neck, adenoid facies, long face, facial swelling, face roundedness, lip incompetence, ptosis, eye bags, receding jaw, malocclusion, facial retrusion, maxillomandibular insufficiency, retrognathia, micrognathia, overbite, narrow nasal passages, deviated septum, tired or fatigued appearance, or periorbital edema.

18. The system of claim 16, further comprising accessing non-visual data that corresponds to one or more biological characteristics of the subject,
wherein providing the N-dimensional vector as input to the machine learning model comprises:
providing N-dimensional vector to a first type of machine learning model; and providing information representing the non-visual data to a second type of machine learning model;

wherein providing the N-dimensional vector to the first type of machine learning model comprises:

providing the N-dimensional vector to a convolutional neural network (CNN), and wherein providing the information representing the non-visual data to the second type of machine learning model comprises:

providing the information representing the non-visual data to a recurrent neural network (RNN), wherein the operations comprise:

providing (i) output from the first type of machine learning model and (ii) output from the second type of machine learning model to a decoder model trained to identify the sleep apnea condition using outputs from the first and second types of machine learning models, wherein obtaining, as the output of the machine learning model, the likelihood of the sleep apnea condition of the subject comprises:

obtaining an output of the decoder model that indicates the likelihood of the sleep apnea condition of the subject, wherein the operations comprise:

generating a first embedding representing at least a portion of (i) the first visual data, (ii) the second visual data, and (iii) the third visual data;

generating a second embedding representing at least a portion of the non-visual data; and generating a fused data set that combines the first embedding and the second embedding, wherein providing the N-dimensional vector as input to machine learning model that is trained to identify the sleep apnea condition comprises providing the fused data set to the machine learning model, and wherein the output of the machine learning model is based on processing of the fused data set by the machine learning model.

19. The system of claim 16, wherein the operations comprise:

accessing data representing an oral cavity of the subject, the data comprising representation of at least one of lower teeth, upper teeth, habitual occlusion, tongue, upper palette, or oropharyngeal region; and determining, using the data representing the oral cavity of the subject, at least one of a high arched palate, enlarged tonsils, adenoids or long uvula, scalloped tongue, macroglossia, malocclusion, overbite, underbite, crossbite, crowding, gapped teeth, open bite, overjet, abnormal eruption, a Mallampati class, or bruxism, wherein the information indicating at least one of a high arched palate, enlarged tonsils, adenoids or long uvula, scalloped tongue, macroglossia, malocclusion, overbite, underbite, crossbite, crowding, gapped teeth, open bite, overjet, abnormal eruption, a Mallampati class, or bruxism is additionally provided as input to the machine learning model.

20. The system of claim 16, wherein computing the estimated pose of the head of the subject using the three-dimensional face mesh comprises:

providing the three-dimensional face mesh to a second machine learning model that is trained to estimate a pose of a subject head or a rule-based engine that estimates a head pose.

21. The system of claim 16, wherein identifying the search region comprises:

identifying, using the three-dimensional face mesh, a mid-facial axis that divides a craniofacial region of the subject into two substantially symmetric halves; and using an orientation of the mid-facial axis to define a parameter for a line-fitting process performed within the search region.

22. The system of claim 16, wherein the machine learning model is further trained using a training library comprising labeled ground truth images that represent silhouettes in an anterior cervical region and fiducial features corresponding to menton and cricoid elements in the anterior cervical region of the training subjects.

23. One or more non-transitory computer storage media encoded with computer program instructions that when executed by one or more computers cause the one or more computers to perform operations comprising:

accessing at least one of (i) first visual data representing a frontal view of a head of a subject, (ii) second visual data representing a side view of the head of the subject, or (iii) third visual data representing an upward looking view of the head of the subject;

fitting a three-dimensional face mesh comprising a plurality of vertices, each vertex of the plurality of vertices associated with three-dimensional coordinates, to at least one of (i) the first visual data, (ii) the second visual data, or (iii) the third visual data;

computing, using the three-dimensional face mesh, an estimated pose of the head of the subject, wherein the estimated pose comprises at least one of a roll angle, a pitch angle, or a yaw angle of the head;

identifying, using the three-dimensional face mesh and the estimated pose of the head of the subject, a search region corresponding to at least one of a craniofacial region or an anterior cervical region of the head of the subject;

determining, from within the search region, a plurality of quantitative measurements of at least one of the craniofacial region or the anterior cervical region, wherein the plurality of quantitative measurements are determined from anatomical landmarks localized within the search region based on the estimated pose and geometric relationships specified by the three-dimensional face mesh;

generating, using at least the plurality of quantitative measurements, an N-dimensional vector, wherein N represents a number of the quantitative measurements;

providing the N-dimensional vector as input to a machine learning model that is trained, using at least one of craniofacial region or anterior cervical region measurements from a plurality of training subjects having known sleep apnea diagnoses, to identify a sleep apnea condition;

obtaining, as an output of the machine learning model, a likelihood of the sleep apnea condition of the subject, wherein the likelihood of the sleep apnea condition is generated by the machine learning model based on processing the N-dimensional vector generated using at least the plurality of quantitative measurements provided as input to the machine learning model;

in response to obtaining the output of the machine learning model indicating that the likelihood of the sleep apnea condition satisfies a threshold, generating attribution data identifying one or more anatomical features of the subject attributed as underlying causes of the sleep apnea condition, wherein the one or more anatomical features are selected from at least one of retrognathia, micrognathia, maxillomandibular insufficiency, enlarged neck circumference, or facial retrusion; and transmitting, to an electronic device, a signal comprising information corresponding to the likelihood of the sleep apnea condition of the subject, wherein the signal is configured to display information representing a potential sleep apnea condition of the subject and recommendation data for at least one therapeutic intervention selected based on the attribution data.

* * * * *